(12) United States Patent
Epshtein et al.

(10) Patent No.: US 8,703,124 B2
(45) Date of Patent: Apr. 22, 2014

(54) COMBINATION PHARMACEUTICAL COMPOSITION AND METHODS OF TREATING DISEASES OR CONDITIONS ASSOCIATED WITH THE CARDIOVASCULAR SYSTEM

(75) Inventors: Oleg Iliich Epshtein, Moscow (RU); Svetlana Alexandrovna Sergeeva, Moscow (RU); Liudmila Fyodorovna Dolgovyh, Chelvabinsk (RU); Vladimir Ivanovich Petrov, Volgograd (RU)

(73) Assignee: Oleg I. Epshtein (RU)

( * ) Notice: Subject to any disclaimer, the term of this patent is extended or adjusted under 35 U.S.C. 154(b) by 0 days.

(21) Appl. No.: 13/135,882

(22) Filed: Jul. 15, 2011
(Under 37 CFR 1.47)

(65) Prior Publication Data
US 2012/0251584 A1    Oct. 4, 2012

(30) Foreign Application Priority Data

| Jul. 15, 2010 | (RU) | ................................ | 2010129290 |
| Jul. 15, 2010 | (RU) | ................................ | 2010129291 |
| Jul. 15, 2010 | (RU) | ................................ | 2010129292 |
| Mar. 17, 2011 | (RU) | ................................ | 2011110106 |

(51) Int. Cl.
*A61K 39/395*    (2006.01)

(52) U.S. Cl.
USPC .................................................... 424/130.1

(58) Field of Classification Search
None
See application file for complete search history.

(56) References Cited

FOREIGN PATENT DOCUMENTS

| EP | 1295606 A1 | 6/2003 |
| EP | 1466622 A1 | 10/2004 |

OTHER PUBLICATIONS

Wikipedia, accessed at en.wikipedia.org/wiki/Isoprenaline on Nov. 20, 2012, 3 pages.*

Petrov et al.: "Pharmacodynamics of Kardos Administered as Monotherapy and in Combination with Hypothiazide and Enalapril in Grade I-II Arterial Hypertension", Bulletin of Experimental Biology and Medicine, vol. 148, No. 2 Aug. 1, 2009, pp. 335-336.
Tiurenkov, I.N. et al.: "Comparison of the Cardioprotective Effects of Cardos and Losartan in Rats with Experimental Chronic Cardiac Insufficiency", Bulletin of Experimental Biology and Medicine, Kluwer Academic Publishers-Plenum Publishers, NE, vol. 143, No. 4, Apr. 1, 2007.
Zhavbert, E.S. et al.: "Evaluation of the Efficiency and Safety of Combined Treatment with Impaza and Nitrates in CHD Patients with Erectile Dysfunction", Bulletin of Experimental Biology and Medicine, vol. 148, No. 2, Aug. 1, 2009, pp. 325-327.
Shang, A. et al.: "Are the Clinical Effects of Homeopathy Placebo Effects? Comparative Study of Placebo-Controlled Trials of Homeopathy and Allopathy", The Lancet, Lancet Limited. GB, vol. 336, No. 9487, Aug. 27, 2005, pp. 726-732.
Jonas, Wayne B. et al.: "A Critical Overview of Homeopathy", Annals of Internal Medicine, New York, NY; U.S., vol. 138, No. 5, Mar. 4, 2003, pp. 393-399.
Vickers, A.J: "Clinical Trials of Homeopathy and Placebo: Analysis of a Scientific Debate", Journal of Alternative and Complementary Medicine, Mary Ann Liebert, New York, NY; U.S. vol. 6, No. 1, Feb. 1, 2000, pp. 49-56.
Anonymous: "Vegetovascular Dystonia—An Expert Response", www.wemove.org, Feb. 27, 2005 Retrieved from the Internet: URL:http//www.wemove.org/forum/ubbthreads.php/topics/2071/Vegetovascular_dystonia_An_Exp [Retrieved on Jan. 19, 2012] See "Response", especially first sentence.
Notification of Transmittal of International Search Report and Written Opinion dated Feb. 14, 2012 for corresponding International Patent Application No. PCT/IB2011/002391.
International Search Report dated Feb. 14, 2012 for corresponding International Patent Application No. PCT/IB2011/002391.
Written Opinion of the International Searching Authority for corresponding International Patent Application No. PCT/IB2011/002391.

* cited by examiner

*Primary Examiner* — Ilia Ouspenski
(74) *Attorney, Agent, or Firm* — Pergament Gilman & Cepeda LLP

(57) ABSTRACT

The present application provides a pharmaceutical composition for administration to a patient suffering from at least one symptom of a cardiovascular condition, the composition comprising a) an activated-potentiated form of an antibody to angiotensin II AT1 receptor, and b) an activated-potentiated form of an antibody to endothelial NO-synthase.

83 Claims, No Drawings

SEQUENCE LISTING

<160> NUMBER OF SEQ ID NOS: 15

<210> SEQ ID NO 1
<211> LENGTH: 413
<212> TYPE: PRT
<213> ORGANISM: Homo sapiens
<220> FEATURE:
<221> NAME/KEY: SOURCE
<222> LOCATION: 1..413
<223> OTHER INFORMATION: /mol_type="protein"
      /organism="Homo sapiens"

<400> SEQUENCE: 1

Ser Pro Pro Ala Gly Thr Arg His Met Ala Asn Thr Tyr Pro Glu Ala
1               5                   10                  15

Asn Gly Ile Thr Glu Asn Ser Ile Asn Ile Ile Arg Glu Cys Glu Pro
            20                  25                  30

Thr Arg Ser His Met Ser Ala Pro Ile Glu Asn Ser Gly Asn Ala Gly
        35                  40                  45

Thr Arg Pro Glu Ser Val Met Ile Leu Asn Ser Ser Thr Glu Asp Gly
    50                  55                  60

Ile Lys Arg Ile Gln Asp Asp Cys Pro Lys Ala Gly Arg His Asn Tyr
65                  70                  75                  80

Ile Phe Val Met Ile Pro Thr Leu Tyr Ser Ile Phe Val Val Gly
                85                  90                  95

Ile Phe Gly Asn Ser Leu Val Val Ile Val Ile Tyr Phe Tyr Met Lys
                100                 105                 110

Leu Lys Thr Val Ala Ser Val Phe Leu Leu Asn Leu Ala Leu Ala Asp
            115                 120                 125

Leu Cys Phe Leu Leu Thr Leu Pro Leu Trp Ala Val Tyr Thr Ala Met
130                 135                 140

Glu Tyr Arg Trp Pro Phe Gly Asn Tyr Leu Cys Lys Ile Ala Ser Ala
145                 150                 155                 160

Ser Val Ser Phe Asn Leu Tyr Ala Ser Val Phe Leu Leu Thr Cys Leu
                165                 170                 175

Ser Ile Asp Arg Tyr Leu Ala Ile Val His Pro Met Lys Ser Arg Leu
            180                 185                 190

Arg Arg Thr Met Leu Val Ala Lys Val Thr Cys Ile Ile Ile Trp Leu
        195                 200                 205

Leu Ala Gly Leu Ala Ser Leu Pro Ala Ile Ile His Arg Asn Val Phe
    210                 215                 220

Phe Ile Glu Asn Thr Asn Ile Thr Val Cys Ala Phe His Tyr Glu Ser
225                 230                 235                 240

Gln Asn Ser Thr Leu Pro Ile Gly Leu Gly Leu Thr Lys Asn Ile Leu
                245                 250                 255

Gly Phe Leu Phe Pro Phe Leu Ile Ile Leu Thr Ser Tyr Thr Leu Ile
                260                 265                 270

Trp Lys Ala Leu Lys Lys Ala Tyr Glu Ile Gln Lys Asn Lys Pro Arg
            275                 280                 285

Asn Asp Asp Ile Phe Lys Ile Ile Met Ala Ile Val Leu Phe Phe Phe
        290                 295                 300

Phe Ser Trp Ile Pro His Gln Ile Phe Thr Phe Leu Asp Val Leu Ile
305                 310                 315                 320

Gln Leu Gly Ile Ile Arg Asp Cys Arg Ile Ala Asp Ile Val Asp Thr
                325                 330                 335

```
Ala Met Pro Ile Thr Ile Cys Ile Ala Tyr Phe Asn Asn Cys Leu Asn
            340                 345                 350

Pro Leu Phe Tyr Gly Phe Leu Gly Lys Lys Phe Lys Arg Tyr Phe Leu
            355                 360                 365

Gln Leu Leu Lys Tyr Ile Pro Pro Lys Ala Lys Ser His Ser Asn Leu
            370                 375                 380

Ser Thr Lys Met Ser Thr Leu Ser Tyr Arg Pro Ser Asp Asn Val Ser
385                 390                 395                 400

Ser Ser Thr Lys Lys Pro Ala Pro Cys Phe Glu Val Glu
            405                 410

<210> SEQ ID NO 2
<211> LENGTH: 54
<212> TYPE: PRT
<213> ORGANISM: Homo sapiens
<220> FEATURE:
<221> NAME/KEY: SOURCE
<222> LOCATION: 1..54
<223> OTHER INFORMATION: /mol_type="protein"
      /organism="Homo sapiens"

<400> SEQUENCE: 2

Gly Lys Lys Phe Lys Arg Tyr Phe Leu Gln Leu Leu Lys Tyr Ile Pro
1               5                   10                  15

Pro Lys Ala Lys Ser His Ser Asn Leu Ser Thr Lys Met Ser Thr Leu
            20                  25                  30

Ser Tyr Arg Pro Ser Asp Asn Val Ser Ser Ser Thr Lys Lys Pro Ala
        35                  40                  45

Pro Cys Phe Glu Val Glu
    50

<210> SEQ ID NO 3
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 3

Gln Leu Leu Lys Tyr Ile Pro Pro Lys Ala
1               5                   10

<210> SEQ ID NO 4
<211> LENGTH: 29
<212> TYPE: PRT
<213> ORGANISM: Homo sapiens
<220> FEATURE:
<221> NAME/KEY: SOURCE
<222> LOCATION: 1..29
<223> OTHER INFORMATION: /mol_type="protein"
      /organism="Homo sapiens"

<400> SEQUENCE: 4

Ser Asn Leu Ser Thr Lys Met Ser Thr Leu Ser Tyr Arg Pro Ser Asp
1               5                   10                  15

Asn Val Ser Ser Ser Thr Lys Lys Pro Ala Pro Cys Phe
            20                  25

<210> SEQ ID NO 5
<211> LENGTH: 55
<212> TYPE: PRT
<213> ORGANISM: artificial sequences
```

```
<220> FEATURE:
<221> NAME/KEY: SOURCE
<222> LOCATION: 1..55
<223> OTHER INFORMATION: /mol_type="protein"
      /note="360-412 aa of human AT1 receptor with added N-terminal Cys"
      /organism="artificial sequences"

<400> SEQUENCE: 5

Cys Gly Lys Lys Phe Lys Arg Tyr Phe Leu Gln Leu Leu Lys Tyr Ile
1               5                   10                  15

Pro Pro Lys Ala Lys Ser His Ser Asn Leu Ser Thr Lys Met Ser Thr
            20                  25                  30

Leu Ser Tyr Arg Pro Ser Asp Asn Val Ser Ser Thr Lys Lys Pro
        35                  40                  45

Ala Pro Cys Phe Glu Val Glu
    50                  55

<210> SEQ ID NO 6
<211> LENGTH: 11
<212> TYPE: PRT
<213> ORGANISM: artificial sequences
<220> FEATURE:
<221> NAME/KEY: SOURCE
<222> LOCATION: 1..11
<223> OTHER INFORMATION: /mol_type="protein"
      /note="369-378 aa of human AT1 receptor with N-terminal added
      cystein"/organism="artificial sequences"

<400> SEQUENCE: 6

Cys Gln Leu Leu Lys Tyr Ile Pro Pro Lys Ala
1               5                   10

<210> SEQ ID NO 7
<211> LENGTH: 30
<212> TYPE: PRT
<213> ORGANISM: artificial sequences
<220> FEATURE:
<221> NAME/KEY: SOURCE
<222> LOCATION: 1..30
<223> OTHER INFORMATION: /mol_type="protein"
      /note="382-410 human AT1 receptor with N- terminal added Cys"
      /organism="artificial sequences"

<400> SEQUENCE: 7

Cys Ser Asn Leu Ser Thr Lys Met Ser Thr Leu Ser Tyr Arg Pro Ser
1               5                   10                  15

Asp Asn Val Ser Ser Ser Thr Lys Lys Pro Ala Pro Cys Phe
            20                  25                  30

<210> SEQ ID NO 8
<211> LENGTH: 1205
<212> TYPE: PRT
<213> ORGANISM: Bos taurus
<220> FEATURE:
<221> NAME/KEY: SOURCE
<222> LOCATION: 1..1205
<223> OTHER INFORMATION: /mol_type="protein"
      /organism="Bos taurus"

<400> SEQUENCE: 8

Met Gly Asn Leu Lys Ser Val Gly Gln Glu Pro Gly Pro Pro Cys Gly
1               5                   10                  15

Leu Gly Leu Gly Leu Gly Leu Gly Leu Cys Gly Lys Gln Gly Pro Ala
            20                  25                  30

Ser Pro Ala Pro Glu Pro Ser Arg Ala Pro Ala Pro Ala Thr Pro His
        35                  40                  45
```

-continued

```
Ala Pro Asp His Ser Pro Ala Pro Asn Ser Pro Thr Leu Thr Arg Pro
 50                  55                  60

Pro Glu Gly Pro Lys Phe Pro Arg Val Lys Asn Trp Glu Leu Gly Ser
 65                  70                  75                  80

Ile Thr Tyr Asp Thr Leu Cys Ala Gln Ser Gln Gln Asp Gly Pro Cys
                 85                  90                  95

Thr Pro Arg Cys Cys Leu Gly Ser Leu Val Leu Pro Arg Lys Leu Gln
            100                 105                 110

Thr Arg Pro Ser Pro Gly Pro Pro Ala Glu Gln Leu Leu Ser Gln
        115                 120                 125

Ala Arg Asp Phe Ile Asn Gln Tyr Tyr Ser Ser Ile Lys Arg Ser Gly
130                 135                 140

Ser Gln Ala His Glu Glu Arg Leu Gln Glu Val Glu Ala Glu Val Ala
145                 150                 155                 160

Ser Thr Gly Thr Tyr His Leu Arg Glu Ser Glu Leu Val Phe Gly Ala
                165                 170                 175

Lys Gln Ala Trp Arg Asn Ala Pro Arg Cys Val Gly Arg Ile Gln Trp
            180                 185                 190

Gly Lys Leu Gln Val Phe Asp Ala Arg Asp Cys Ser Ser Ala Gln Glu
        195                 200                 205

Met Phe Thr Tyr Ile Cys Asn His Ile Lys Tyr Ala Thr Asn Arg Gly
210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                245                 250                 255

Arg Gln Gln Asp Gly Ser Val Arg Gly Asp Pro Ala Asn Val Glu Ile
            260                 265                 270

Thr Glu Leu Cys Ile Gln His Gly Trp Thr Pro Gly Asn Gly Arg Phe
        275                 280                 285

Asp Val Leu Pro Leu Leu Leu Gln Ala Pro Asp Glu Ala Pro Glu Leu
290                 295                 300

Phe Val Leu Pro Pro Glu Leu Val Leu Glu Val Pro Leu Glu His Pro
305                 310                 315                 320

Thr Leu Glu Trp Phe Ala Ala Leu Gly Leu Arg Trp Tyr Ala Leu Pro
                325                 330                 335

Ala Val Ser Asn Met Leu Leu Glu Ile Gly Gly Leu Glu Phe Ser Ala
            340                 345                 350

Ala Pro Phe Ser Gly Trp Tyr Met Ser Thr Glu Ile Gly Thr Arg Asn
        355                 360                 365

Leu Cys Asp Pro His Arg Tyr Asn Ile Leu Glu Asp Val Ala Val Cys
370                 375                 380

Met Asp Leu Asp Thr Arg Thr Thr Ser Ser Leu Trp Lys Asp Lys Ala
385                 390                 395                 400

Ala Val Glu Ile Asn Leu Ala Val Leu His Ser Phe Gln Leu Ala Lys
                405                 410                 415

Val Thr Ile Val Asp His His Ala Ala Thr Val Ser Phe Met Lys His
            420                 425                 430

Leu Asp Asn Glu Gln Lys Ala Arg Gly Gly Cys Pro Ala Asp Trp Ala
        435                 440                 445

Trp Ile Val Pro Pro Ile Ser Gly Ser Leu Thr Pro Val Phe His Gln
450                 455                 460

Glu Met Val Asn Tyr Ile Leu Ser Pro Ala Phe Arg Tyr Gln Pro Asp
465                 470                 475                 480
```

-continued

```
Pro Trp Lys Gly Ser Ala Thr Lys Gly Ala Gly Ile Thr Arg Lys Lys
                485                 490                 495
Thr Phe Lys Glu Val Ala Asn Ala Val Lys Ile Ser Ala Ser Leu Met
                500                 505                 510
Gly Thr Leu Met Ala Lys Arg Val Lys Ala Thr Ile Leu Tyr Ala Ser
                515                 520                 525
Glu Thr Gly Arg Ala Gln Ser Tyr Ala Gln Gln Leu Gly Arg Leu Phe
            530                 535                 540
Arg Lys Ala Phe Asp Pro Arg Val Leu Cys Met Asp Glu Tyr Asp Val
545                 550                 555                 560
Val Ser Leu Glu His Glu Ala Leu Val Leu Val Val Thr Ser Thr Phe
                565                 570                 575
Gly Asn Gly Asp Pro Pro Glu Asn Gly Glu Ser Phe Ala Ala Ala Leu
                580                 585                 590
Met Glu Met Ser Gly Pro Tyr Asn Ser Ser Pro Arg Pro Glu Gln His
            595                 600                 605
Lys Ser Tyr Lys Ile Arg Phe Asn Ser Val Ser Cys Ser Asp Pro Leu
            610                 615                 620
Val Ser Ser Trp Arg Arg Lys Arg Lys Glu Ser Ser Asn Thr Asp Ser
625                 630                 635                 640
Ala Gly Ala Leu Gly Thr Leu Arg Phe Cys Val Phe Gly Leu Gly Ser
                645                 650                 655
Arg Ala Tyr Pro His Phe Cys Ala Phe Ala Arg Ala Val Asp Thr Arg
                660                 665                 670
Leu Glu Glu Leu Gly Gly Glu Arg Leu Leu Gln Leu Gly Gln Gly Asp
            675                 680                 685
Glu Leu Cys Gly Gln Glu Glu Ala Phe Arg Gly Trp Ala Lys Ala Ala
            690                 695                 700
Phe Gln Ala Ser Cys Glu Thr Phe Cys Val Gly Glu Glu Ala Lys Ala
705                 710                 715                 720
Ala Ala Gln Asp Ile Phe Ser Pro Lys Arg Ser Trp Lys Arg Gln Arg
                725                 730                 735
Tyr Arg Leu Ser Thr Gln Ala Glu Gly Leu Gln Leu Leu Pro Gly Leu
                740                 745                 750
Ile His Val His Arg Arg Lys Met Phe Gln Ala Thr Val Leu Ser Val
                755                 760                 765
Glu Asn Leu Gln Ser Ser Lys Ser Thr Arg Ala Thr Ile Leu Val Arg
            770                 775                 780
Leu Asp Thr Ala Gly Gln Glu Gly Leu Gln Tyr Gln Pro Gly Asp His
785                 790                 795                 800
Ile Gly Ile Cys Pro Pro Asn Arg Pro Gly Leu Val Glu Ala Leu Leu
                805                 810                 815
Ser Arg Val Glu Asp Pro Pro Pro Thr Glu Ser Val Ala Val Glu
                820                 825                 830
Gln Leu Glu Lys Gly Ser Pro Gly Gly Pro Pro Ser Trp Val Arg
            835                 840                 845
Asp Pro Arg Leu Pro Pro Cys Thr Leu Arg Gln Ala Leu Thr Phe Phe
                850                 855                 860
Leu Asp Ile Thr Ser Pro Pro Ser Pro Arg Leu Leu Arg Leu Leu Ser
865                 870                 875                 880
Thr Leu Ala Glu Glu Pro Ser Glu Gln Gln Glu Leu Glu Thr Leu Ser
                885                 890                 895
Gln Asp Pro Arg Arg Tyr Glu Glu Trp Lys Trp Phe Arg Cys Pro Thr
```

900                 905                 910
Leu Leu Glu Val Leu Glu Gln Phe Pro Ser Val Ala Leu Pro Ala Pro
                915                 920                 925

Leu Leu Leu Thr Gln Leu Pro Leu Leu Gln Pro Arg Tyr Tyr Ser Val
            930                 935                 940

Ser Ser Ala Pro Asn Ala His Pro Gly Glu Val His Leu Thr Val Ala
945                 950                 955                 960

Val Leu Ala Tyr Arg Thr Gln Asp Gly Leu Gly Pro Leu His Tyr Gly
                965                 970                 975

Val Cys Ser Thr Trp Leu Ser Gln Leu Lys Thr Gly Asp Pro Val Pro
            980                 985                 990

Cys Phe Ile Arg Gly Ala Pro Ser Phe Arg Leu Pro Pro Asp Pro Tyr
        995                 1000                1005

Val Pro Cys Ile Leu Val Gly Pro Thr Gly Ile Ala Pro Phe Arg
    1010                1015                1020

Gly Phe Trp Gln Glu Arg Leu His Asp Ile Glu Ser Lys Gly Leu Gln
1025                1030                1035                1040

Pro Ala Pro Met Thr Leu Val Phe Gly Cys Arg Cys Ser Gln Leu Asp
                1045                1050                1055

His Leu Tyr Arg Asp Glu Val Gln Asp Ala Gln Glu Arg Gly Val Phe
            1060                1065                1070

Gly Arg Val Leu Thr Ala Phe Ser Arg Glu Pro Asp Ser Pro Lys Thr
        1075                1080                1085

Tyr Val Gln Asp Ile Leu Arg Thr Gln Leu Ala Ala Glu Val His Arg
    1090                1095                1100

Val Leu Cys Leu Glu Arg Gly His Met Phe Val Cys Gly Asp Val Thr
1105                1110                1115                1120

Met Ala Thr Ser Val Leu Gln Thr Val Gln Arg Ile Leu Ala Thr Glu
                1125                1130                1135

Gly Asp Met Glu Leu Asp Glu Ala Gly Asp Val Ile Gly Val Leu Arg
            1140                1145                1150

Asp Gln Gln Arg Tyr His Glu Asp Ile Phe Gly Leu Thr Leu Arg Thr
        1155                1160                1165

Gln Glu Val Thr Ser Arg Ile Arg Thr Gln Ser Phe Ser Leu Gln Glu
    1170                1175                1180

Arg His Leu Arg Gly Ala Val Pro Trp Ala Phe Asp Pro Pro Gly Pro
1185                1190                1195                1200

Asp Thr Pro Gly Pro
            1205

<210> SEQ ID NO 9
<211> LENGTH: 1203
<212> TYPE: PRT
<213> ORGANISM: Homo sapiens
<220> FEATURE:
<221> NAME/KEY: SOURCE
<222> LOCATION: 1..1203
<223> OTHER INFORMATION: /mol_type="protein"
      /organism="Homo sapiens"

<400> SEQUENCE: 9

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
            20                  25                  30

Thr Pro Ala Pro Glu Pro Ser Arg Ala Pro Ala Ser Leu Leu Pro Pro
        35                  40                  45

```
Ala Pro Glu His Ser Pro Pro Ser Ser Pro Leu Thr Gln Pro Pro Glu
    50                  55                  60

Gly Pro Lys Phe Pro Arg Val Lys Asn Trp Glu Val Gly Ser Ile Thr
 65                  70                  75                  80

Tyr Asp Thr Leu Ser Ala Gln Ala Gln Gln Asp Gly Pro Cys Thr Pro
                     85                  90                  95

Arg Arg Cys Leu Gly Ser Leu Val Phe Pro Arg Lys Leu Gln Gly Arg
                100                 105                 110

Pro Ser Pro Gly Pro Pro Ala Pro Glu Gln Leu Leu Ser Gln Ala Arg
                115                 120                 125

Asp Phe Ile Asn Gln Tyr Tyr Ser Ser Ile Lys Arg Ser Gly Ser Gln
    130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
                180                 185                 190

Leu Gln Val Phe Asp Ala Arg Asp Cys Arg Ser Ala Gln Glu Met Phe
    195                 200                 205

Thr Tyr Ile Cys Asn His Ile Lys Tyr Ala Thr Asn Arg Gly Asn Leu
210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
                260                 265                 270

Leu Cys Ile Gln His Gly Trp Thr Pro Gly Asn Gly Arg Phe Asp Val
    275                 280                 285

Leu Pro Leu Leu Leu Gln Ala Pro Asp Glu Pro Pro Glu Leu Phe Leu
    290                 295                 300

Leu Pro Pro Glu Leu Val Leu Glu Val Pro Leu Glu His Pro Thr Leu
305                 310                 315                 320

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
                340                 345                 350

Phe Ser Gly Trp Tyr Met Ser Thr Glu Ile Gly Thr Arg Asn Leu Cys
    355                 360                 365

Asp Pro His Arg Tyr Asn Ile Leu Glu Asp Val Ala Val Cys Met Asp
    370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
                420                 425                 430

Asn Glu Gln Lys Ala Arg Gly Gly Cys Pro Ala Asp Trp Ala Trp Ile
    435                 440                 445

Val Pro Pro Ile Ser Gly Ser Leu Thr Pro Val Phe His Gln Glu Met
    450                 455                 460

Val Asn Tyr Phe Leu Ser Pro Ala Phe Arg Tyr Gln Pro Asp Pro Trp
```

```
            465                 470                 475                 480
Lys Gly Ser Ala Ala Lys Gly Thr Gly Ile Thr Arg Lys Lys Thr Phe
                    485                 490                 495

Lys Glu Val Ala Asn Ala Val Lys Ile Ser Ala Ser Leu Met Gly Thr
                500                 505                 510

Val Met Ala Lys Arg Val Lys Ala Thr Ile Leu Tyr Gly Ser Glu Thr
                515                 520                 525

Gly Arg Ala Gln Ser Tyr Ala Gln Gln Leu Gly Arg Leu Phe Arg Lys
            530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
                580                 585                 590

Met Ser Gly Pro Tyr Asn Ser Ser Pro Arg Pro Glu Gln His Lys Ser
            595                 600                 605

Tyr Lys Ile Arg Phe Asn Ser Ile Ser Cys Ser Asp Pro Leu Val Ser
            610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
                660                 665                 670

Glu Leu Gly Gly Glu Arg Leu Leu Gln Leu Gly Gln Gly Asp Glu Leu
            675                 680                 685

Cys Gly Gln Glu Glu Ala Phe Arg Gly Trp Ala Gln Ala Ala Phe Gln
690                 695                 700

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
                725                 730                 735

Leu Ser Ala Gln Ala Glu Gly Leu Gln Leu Leu Pro Gly Leu Ile His
            740                 745                 750

Val His Arg Arg Lys Met Phe Gln Ala Thr Ile Arg Ser Val Glu Asn
                755                 760                 765

Leu Gln Ser Ser Lys Ser Thr Arg Ala Thr Ile Leu Val Arg Leu Asp
            770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
                820                 825                 830

Glu Lys Gly Ser Pro Gly Gly Pro Pro Gly Trp Val Arg Asp Pro
            835                 840                 845

Arg Leu Pro Pro Cys Thr Leu Arg Gln Ala Leu Thr Phe Phe Leu Asp
            850                 855                 860

Ile Thr Ser Pro Pro Ser Pro Gln Leu Leu Arg Leu Leu Ser Thr Leu
865                 870                 875                 880

Ala Glu Glu Pro Arg Glu Gln Gln Glu Leu Glu Ala Leu Ser Gln Asp
                885                 890                 895
```

```
Pro Arg Arg Tyr Glu Glu Trp Lys Trp Phe Arg Cys Pro Thr Leu Leu
            900                 905                 910

Glu Val Leu Glu Gln Phe Pro Ser Val Ala Leu Pro Ala Pro Leu Leu
            915                 920                 925

Leu Thr Gln Leu Pro Leu Leu Gln Pro Arg Tyr Tyr Ser Val Ser Ser
            930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
            965                 970                 975

Ser Thr Trp Leu Ser Gln Leu Lys Pro Gly Asp Pro Val Pro Cys Phe
            980                 985                 990

Ile Arg Gly Ala Pro Ser Phe Arg Leu Pro Pro Asp Pro Ser Leu Pro
            995                 1000                1005

Cys Ile Leu Val Gly Pro Gly Thr Gly Ile Ala Pro Phe Arg Gly Phe
        1010                1015                1020

Trp Gln Glu Arg Leu His Asp Ile Glu Ser Lys Gly Leu Gln Pro Thr
1025                1030                1035                1040

Pro Met Thr Leu Val Phe Gly Cys Arg Cys Ser Gln Leu Asp His Leu
            1045                1050                1055

Tyr Arg Asp Glu Val Gln Asn Ala Gln Gln Arg Gly Val Phe Gly Arg
            1060                1065                1070

Val Leu Thr Ala Phe Ser Arg Glu Pro Asp Asn Pro Lys Thr Tyr Val
        1075                1080                1085

Gln Asp Ile Leu Arg Thr Glu Leu Ala Ala Glu Val His Arg Val Leu
        1090                1095                1100

Cys Leu Glu Arg Gly His Met Phe Val Cys Gly Asp Val Thr Met Ala
1105                1110                1115                1120

Thr Asn Val Leu Gln Thr Val Gln Arg Ile Leu Ala Thr Glu Gly Asp
            1125                1130                1135

Met Glu Leu Asp Glu Ala Gly Asp Val Ile Gly Val Leu Arg Asp Gln
            1140                1145                1150

Gln Arg Tyr His Glu Asp Ile Phe Gly Leu Thr Leu Arg Thr Gln Glu
            1155                1160                1165

Val Thr Ser Arg Ile Arg Thr Gln Ser Phe Ser Leu Gln Glu Arg Gln
        1170                1175                1180

Leu Arg Gly Ala Val Pro Trp Ala Phe Asp Pro Pro Gly Ser Asp Thr
1185                1190                1195                1200

Asn Ser Pro

<210> SEQ ID NO 10
<211> LENGTH: 4
<212> TYPE: PRT
<213> ORGANISM: Bos taurus
<220> FEATURE:
<221> NAME/KEY: SOURCE
<222> LOCATION: 1..4
<223> OTHER INFORMATION: /mol_type="protein"
     /organism="Bos taurus"

<400> SEQUENCE: 10

Pro Trp Ala Phe
1

<210> SEQ ID NO 11
<211> LENGTH: 4
<212> TYPE: PRT
<213> ORGANISM: Bos taurus
```

```
<220> FEATURE:
<221> NAME/KEY: SOURCE
<222> LOCATION: 1..4
<223> OTHER INFORMATION: /mol_type="protein"
      /organism="Bos taurus"

<400> SEQUENCE: 11

Gly Ala Val Pro
1

<210> SEQ ID NO 12
<211> LENGTH: 21
<212> TYPE: PRT
<213> ORGANISM: Bos taurus
<220> FEATURE:
<221> NAME/KEY: SOURCE
<222> LOCATION: 1..21
<223> OTHER INFORMATION: /mol_type="protein"
      /organism="Bos taurus"

<400> SEQUENCE: 12

Arg His Leu Arg Gly Ala Val Pro Trp Ala Phe Asp Pro Pro Gly Pro
1               5                   10                  15

Asp Thr Pro Gly Pro
            20

<210> SEQ ID NO 13
<211> LENGTH: 12
<212> TYPE: PRT
<213> ORGANISM: Bos taurus
<220> FEATURE:
<221> NAME/KEY: SOURCE
<222> LOCATION: 1..12
<223> OTHER INFORMATION: /mol_type="protein"
      /organism="Bos taurus"

<400> SEQUENCE: 13

Ala Phe Asp Pro Pro Gly Pro Asp Thr Pro Gly Pro
1               5                   10

<210> SEQ ID NO 14
<211> LENGTH: 11
<212> TYPE: PRT
<213> ORGANISM: Bos taurus
<220> FEATURE:
<221> NAME/KEY: SOURCE
<222> LOCATION: 1..11
<223> OTHER INFORMATION: /mol_type="protein"
      /organism="Bos taurus"

<400> SEQUENCE: 14

His Leu Arg Gly Ala Val Pro Trp Ala Phe Asp
1               5                   10

<210> SEQ ID NO 15
<211> LENGTH: 20
<212> TYPE: PRT
<213> ORGANISM: Bos taurus
<220> FEATURE:
<221> NAME/KEY: SOURCE
<222> LOCATION: 1..20
<223> OTHER INFORMATION: /mol_type="protein"
      /organism="Bos taurus"
```

```
<400> SEQUENCE: 15

His Leu Arg Gly Ala Val Pro Trp Ala Phe Asp Pro Pro Gly Pro Asp
1               5                   10                  15

Thr Pro Gly Pro
            20
```

US 8,703,124 B2

COMBINATION PHARMACEUTICAL COMPOSITION AND METHODS OF TREATING DISEASES OR CONDITIONS ASSOCIATED WITH THE CARDIOVASCULAR SYSTEM

FIELD

The present invention relates to the field of medicine and can be used for the treatment and prevention of diseases of the cardiovascular system.

BACKGROUND

Nitric oxide (NO) is a cellular signaling molecule which plays a role in many biological processes including the relaxation of vascular and non-vascular tissue. Nitric oxide is synthesized from L-arginine by nitric oxide synthase (NO synthase). NO synthase occurs in different isoforms, including a constitutive form (cNOS) and an inducible form (iNOS). The constitutive form is present in normal endothelial cells, neurons and some other tissues. Formation of nitric oxide by the constitutive form in endothelial cells is thought to play an important role in normal blood pressure regulation.

Angiotensin is a protein that causes blood vessels to constrict, and drives blood pressure up and stimulates the release of aldosterone from the adrenal cortex. Angiotensin is part of the renin-angiotensin system (a hormone system that regulates blood pressure and water (fluid) balance) which is a major target for drugs that lower blood pressure. Angiotensin II receptor type 1 (AT1) is believed to mediate the key effects of angiotensin II.

The therapeutic effect of an extremely diluted (or ultra-low) form of antibodies potentized by homeopathic technology has been discovered by the inventor of the present patent application, Dr. Oleg I. Epshtein. U.S. Pat. No. 7,582,294 discloses a medicament for treating Benign Prostatic Hyperplasia or prostatitis by administration of a homeopathically activated form of antibodies to prostate specific antigen (PSA). U.S. Patent Publication No. 2010/0260742 discloses a homeopathically potentized form of antibodies to a C-terminal fragment of the angiotensin II AT1 receptor. The homeopathically potentized form of antibodies to a C-terminal fragment of the angiotensin II AT1 receptor is marketed in the Russian Federation and other countries under the name Kardos®. U.S. Pat. No. 7,700,096 discloses and claims a homeopathically potentized form of antibodies to endothelial NO-synthase. The homeopathically potentized form of antibodies to endothelial NO-synthase is marketed in the Russian Federation and other countries under the name Impaza®.

There is a continuing need for new drug products with desired therapeutic efficacy for treatment of diseases and disorder of the cardiovascular system.

SUMMARY

In one aspect the invention provides a pharmaceutical composition for administration to a patient suffering from at least one symptom of a cardiovascular condition, said composition comprising a) an activated-potentiated form of an antibody to angiotensin II AT1 receptor, and b) an activated-potentiated form of an antibody to endothelial NO-synthase.

In one variant of this aspect of the invention a pharmaceutical composition for administration to a patient suffering from at least one symptom of a cardiovascular condition comprises a) an activated-potentiated form of an antibody to a C-terminal fragment of angiotensin II AT1 receptor, and b) an activated-potentiated form of an antibody to endothelial NO-synthase.

Preferably, the pharmaceutical composition of this aspect is administered to patients with cardiovascular condition(s) associated with a reduced quality of life, wherein the administration of said pharmaceutical composition to said patient improves said quality of life of said patient.

Various variants and embodiments of the pharmaceutical composition are contemplated and provided. They may be used in reference to method aspects and embodiments of the invention. The specific variants and embodiments of this aspect of the invention are set forth in the appended claims. Preferably, the pharmaceutical composition of the invention comprises activated-potentiated forms of polyclonal antibodies. It is also preferred that the process of preparing the pharmaceutical composition of this aspect of the invention includes successive centesimal dilutions coupled with vertical shaking of every dilution.

In another aspect, the invention provides a method of treating a patient suffering from a reduced overall quality of life associated with at least one symptom of a cardiovascular condition, said method comprising administering to said patient a combination of a) an activated-potentiated form of an antibody to angiotensin II AT1 receptor, and b) an activated-potentiated form of an antibody to endothelial NO-synthase, thereby said administration improves said overall quality of life of said patient. Preferably, the invention provides a method of treating a patient suffering from a reduced overall quality of life associated with at least one symptom of a cardiovascular condition, said method comprising administering to said patient a combination of a) an activated-potentiated form of an antibody to a C-terminal fragment of angiotensin II AT1 receptor, and b) an activated-potentiated form of an antibody to endothelial NO-synthase, thereby said administration improves said overall quality of life of said patient. Various variants and embodiments are contemplated. In particular, it is contemplated that the combination of this aspect of the invention is administered concomitantly with administration of an additional therapeutic agent suitable for administration to patients suffering from said at least one symptom of a cardiovascular condition. The non-limiting list of suitable additional agents includes ACE inhibitors, diuretics; β-adrenergic blockers, nitrates, cardiac glycosides, calcium antagonists, hypolipidemic agents, antiaggregants, antihypoxants, and anticoagulants. Bisoprol, enalapril or aspirin are specifically contemplated.

Particularly contemplated is a method of this aspect of the invention in which said patient is administered said composition in the form of a solid unit dosage form comprising said activated-potentiated form of an antibody to a C-terminal fragment of angiotensin II AT1 receptor and said activated-potentiated form of an antibody to endothelial NO-synthase. Preferably, said patient is administered one to two of said unit dosage forms, each administration carried out from once daily to four times daily.

In another aspect, the invention provides a method of treating a patient suffering from chronic heart failure, said method comprising administering to said patient a combination of a) an activated-potentiated form of an antibody to a C-terminal fragment of angiotensin II AT1 receptor, and b) an activated-potentiated form of an antibody to endothelial NO-synthase. Various variants and embodiments are contemplated. In particular, it is contemplated that the combination of this aspect of the invention is administered concomitantly with administration of an additional therapeutic agent suitable for administration to patients suffering from said at least one symptom of a cardiovascular condition. The non-limiting list of suitable additional agents includes ACE inhibitors, diuretics; β-adrenergic blockers, nitrates, cardiac glycosides, calcium antagonists, hypolipidemic agents, antiaggregants, antihypoxants, and anticoagulants. Bisoprol, enalapril or aspirin are specifically contemplated.

Particularly contemplated is a method of this aspect of the invention in which said patient is administered said composition in the form of a solid unit dosage form comprising said activated-potentiated form of an antibody to a C-terminal fragment of angiotensin II AT1 receptor and said activated-potentiated form of an antibody to endothelial NO-synthase. Preferably, said patient is administered one to two of said unit dosage forms, each administration carried out from once daily to four times daily. In accordance with this aspect of the invention, said patient exhibits statistically significant improvement in rigidity parameters of carotid radial artery segments upon said administration. In accordance with this aspect of the invention, said patient exhibits statistically significant improvement in rigidity parameters of carotid femoral artery segments upon said administration. In accordance with this aspect of the invention, said patient exhibits statistically significant reduction in anxiety associated with said chronic heart failure upon said administration. It is particularly contemplated that said administration of said combination leads to a statistically significant improvement in the The Minnesota Living with Heart Failure questionnaire (MLHFQ) score in a suitable population of said patients in reference to the baseline. It is particularly contemplated that said administration of said combination leads to a statistically significant reduction in the Kansas City Cardiomyopathy Questionnaire total Score in a suitable population of said patients in reference to the baseline. It is particularly contemplated that said administration of said combination leads to a statistically significant improvement in a 6-minute walking test score in a suitable population of said patients. It is particularly contemplated that said administration of said combination leads to a statistically significant improvement in the Hospital Anxiety and Depression Scale (HADS) total score in a suitable population of said patients. It is particularly contemplated that said administration of said combination leads to said patient exhibiting statistically significant reduction in depression associated with said chronic heart failure upon said administration.

In another aspect, the invention provides a method of treating a patient suffering from asthenia and/or vegetative-vascular dystonia, said method comprising administering to said patient a combination of a) an activated-potentiated form of an antibody to a C-terminal fragment of angiotensin II AT1 receptor, and b) an activated-potentiated form of an antibody to endothelial NO-synthase. Various variants and embodiments are contemplated. In particular, it is contemplated that the combination of this aspect of the invention is administered concomitantly with administration of an additional therapeutic agent suitable for administration to patients suffering from said at least one symptom of a cardiovascular condition. The non-limiting list of suitable additional agents includes ACE inhibitors, diuretics; β-adrenergic blockers, nitrates, cardiac glycosides, calcium antagonists, hypolipidemic agents, antiaggregants, antihypoxants, and anticoagulants. Bisoprol, enalapril or aspirin are specifically contemplated.

It is particularly contemplated in accordance with this aspect of the invention that said patient exhibits statistically significant improvement in rigidity parameters of carotid radial artery segments upon said administration. It is particularly contemplated that said patient exhibits statistically significant improvement in rigidity parameters of carotid femoral artery segments upon said administration. It is particularly contemplated that said patient exhibits statistically significant reduction in mental asthenia upon said administration. Preferably, said administration of said combination leads to a statistically significant reduction in the mental asthenia by the Multidimensional Fatigue Inventory (MFI-20) scale in a suitable population of said patients in reference to the baseline. Preferably, the administration of the combination drug or medicine in accordance with this aspect of the invention leads to said patient exhibiting statistically significant reduction in general asthenia upon said administration. Preferably, said administration of said combination leads to a statistically significant reduction in the general asthenia by the MFI-20 scale in a suitable population of said patients in reference to the baseline. Preferably, said patient exhibits statistically significant reduction in anxiety associated with said asthenia and/or vegetative vascular dystonia upon said administration. It is preferred that in accordance with this aspect of the invention, said administration of said combination drug or medicine leads to a statistically significant reduction in the trait anxiety as measured by the Spielberg test in a suitable population of said patients in reference to the baseline. Preferably, said patient exhibits statistically significant reduction in depression associated with said asthenia and/or vegetative vascular dystonia upon said administration. It is particularly contemplated that said administration of said combination drug or medicine leads to a statistically significant reduction in depression as measured by the Beck test in a suitable population of said patients in reference to the baseline. Preferably, said patient exhibits statistically significant improvement in brachial artery dilation level upon said administration.

In another aspect, the invention provides a method of treating hypertension comprising administering the combination described herein to a patient in need thereof. Concomitant administration of an additional therapeutic agent selected from the group consisting of ACE inhibitors, diuretics; β-adrenergic blockers, nitrates, cardiac glycosides, calcium antagonists, hypolipidemic agents, antiaggregants, antihypoxants, and anticoagulants is specifically contemplated.

DETAILED DESCRIPTION

The invention is defined with reference to the appended claims. With respect to the claims, the glossary that follows provides the relevant definitions.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')$_2$, Fab', and the like. The singular "antibody" includes plural "antibodies".

The term "activated-potentiated form" or "potentiated form", respectively, with respect to antibodies recited herein is used to denote a product of homeopathic potentization of any initial solution of antibodies. "Homeopathic potentization" denotes the use of methods of homeopathy to impart homeopathic potency to an initial solution of relevant substance. Although not so limited, "homeopathic potentization" may involve, for example, repeated consecutive dilutions combined with external treatment, particularly (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably, water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200. Examples of homeopathic potentization are described in U.S. Pat. Nos. 7,572,441 and 7,582,294, which are incorporated herein by reference in their entirety and for the purpose stated. While the term "activated-potentiated form" is used in the claims, the term "ultra-low doses" is used in the examples. The term "ultra-low doses" became a term of art in the field of art created by study and use of homeopathically diluted and potentized form of substance. The term "ultra-low dose" or "ultra-low doses" is meant as fully supportive and primarily synonymous with the term "activated-potentiated" form used in the claims.

In other words, an antibody is in the "activated-potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. And third, the biological activity exhibited by the "activated-potentiated" form of the antibody cannot be explained by the presence of the molecular form of the antibody in the final product of the homeopathic process.

For example, the activated potentiated form of antibodies may be prepared by subjecting an initial, isolated antibody in a molecular form to consecutive multiple dilutions coupled with an external impact, such as mechanical shaking. The external treatment in the course of concentration reduction may also be accomplished, for example, by exposure to ultrasonic, electromagnetic, or other physical factors. V. Schwabe "Homeopathic medicines", M., 1967, U.S. Pat. Nos. 7,229,648 and 4,311,897, which are incorporated by reference in their entirety and for the purpose stated, describe such processes which are well accepted methods of homeopathic potentiation in the homeopathic art. This procedure gives rise to a uniform decrease in molecular concentration of the initial molecular form of the antibody. This procedure is repeated until the desired homeopathic potency is obtained. For the individual antibody, the required homeopathic potency can be determined by subjecting the intermediate dilutions to biological testing in the desired pharmacological model. Although not so limited, "homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably, water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200 or the mixture of three aqueous or aqueous-alcohol dilutions of the primary matrix solution (mother tincture) of antibodies diluted $100^{12}$, $100^{30}$ and $100^{50}$ times, respectively, which is equivalent to centesimal homeopathic dilutions C12, C30 and C50. Examples of how to obtain the desired potency are also provided, for example, in U.S. Pat. Nos. 7,229,648 and 4,311,897, which are incorporated by reference for the purpose stated. The procedure applicable to the "activated potentiated" form of the antibodies described herein is described in more detail below.

There has been a considerable amount of controversy regarding homeopathic treatment of human subjects. While the present invention relies on accepted homeopathic processes to obtain the "activated-potentiated" form of antibodies, it does not rely solely on homeopathy in human subjects for evidence of activity. It has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. The "activated-potentiated" form of the antibody provided herein are tested for biological activity in well accepted pharmacological models of activity, either in appropriate in vitro experiments, or in vivo in suitable animal models. The experiments provided further below provide evidence of biological activity in such models. The human clinical studies, also provided herein below, inter alia provide evidence that the activity observed in the animal model is well translated to human therapy. The human study also provides evidence of availability of the "activated potentiated" forms described herein to treat specified human diseases or disorders well accepted as pathological conditions in the medical science.

Also, the claimed "activated-potentiated" form of antibody encompasses only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated" form of the antibodies of the present invention is not attributable to the initial molecular form of the antibody. Preferred is the "activated-potentiated" form of antibody in liquid or solid form in which the concentration of the initial molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the initial molecular form of the antibody is below the Avogadro number. In pharmacology of molecular forms of therapeutic substances, it is common practice to create a dose-response curve in which the level of pharmacological response is plotted against the concentration of the active drug administered to the subject or tested in vitro. The minimal level of the drug which produces any detectable response is known as a threshold dose. It is specifically contemplated and preferred that the "activated-potentiated" form of the antibodies contains molecular antibody, if any, at a concentration below the threshold dose for the molecular form of the antibody in the given biological model. The specific compositions described in the appended examples are described with the term ultra-low doses (ULD), which term is not intended to be used in construing the claims of the present application.

The term "cardiovascular condition" denotes disease or disorder of the cardiovascular system in human defined as such in the medical profession. Non-limiting examples of cardiovascular conditions include heart failure, arterial hypertension, and asthenia.

The term "symptom" with respect to "cardiovascular conditions" denotes those manifestations of patients suffering from diseases or disorders of the cardiovascular system that reduce quality of life of such patients. Non-limiting examples of symptoms of cardiovascular conditions that reduce quality of life include anxiety, depression, and walking difficulty.

The term "quality of life" denotes the subjective feeling of well-being of a patient. The quality of life of a patient increases with reduction in or improvement of symptoms. The term "quality of life" is meant to define the collection of symptoms associated with cardiovascular deceases or disorders in a patient population.

The term "MFI-20 scale" refers to "multidimensional fatigue inventory", which is a 20-question inventory questionnaire used to measure the levels of physical, psychological and mental fatigue. It denotes the MFI-20 questionnaire commonly used by those skilled in the art. An example of use of the MFI-20 scale to assess fatigue in patients with chronic heart failure may be found in K. Falk et al., Fatigue and Anaemia in Patients with Chronic Heart Failure, European Journal of Heart Failure, 8, 744-749 (2006), which is incorporated herein by reference.

The term "The Minnesota Living with Heart Failure questionnaire" (MLHFQ), also referred to as the Minnesota questionnaire, refers to a well-established questionnaire commonly used to assess quality of life and levels of anxiety in people with cardiovascular conditions, and heart failure in particular.

The content of the Minnesota questionnaire is representative of the ways cardiovascular conditions, and particularly heart failure, together with appropriate treatments, affect the physical, emotional, social and mental dimensions of quality of life. The questionnaire focuses on questions that assess the impact of frequent physical symptoms—shortness of breath, fatigue, peripheral edema, and sleeping difficulty, and psychological symptoms of anxiety and depression. In addition, the effects of heart failure on physical/social functions including walking, climbing stairs, household work, need to rest, working to earn a living, going places away from home, doing things with family or friends, recreational activities, sexual activities, eating and mental and emotional functions of concentration, memory, loss of self-control, and being a burden to others were incorporated into the measure. Since treatments might have side effects in addition to ameliorating symptoms and functional limitations produced by heart failure, questions about side effects of medications, hospital stays and costs of care are included to help measure the overall impact of a treatment on quality of life. To measure the effects of symptoms, functional limitations, psychological distress on an individual's quality of life, the questionnaire asks each person to indicate using a 6-point, zero to five, Likert scale how much each of 21 facets prevented them from living as they desired. This response format is consistent with the concept of quality of life and allows each individual to weigh each item using a common scale. Therefore, one can look at which items had the most effect and the sum of responses reflects the overall effects of heart failure and treatments on the individual's quality of life. Although the Minnesota Living with Heart Failure Questionnaire incorporates relevant aspects of the key dimensions of quality of life, the questionnaire was not designed to measure any particular dimension separately. Given the conceptual basis for the questionnaire, items on the questionnaire are considered to be 'causal' indicators of quality of life in the sense that they can affect someone's quality of life when they occur, but may not be present when other aspects of heart failure are affecting an individual's quality of life. The total score is taken as the best measure of how cardiovascular condition, and particularly heart failure, and commensurate treatments impact the quality of life.

The term "Kansas City Cardiomyopathy Questionnaire" (KCCQ) or "Kansas Questionnaire" refers to a health-related quality-of-life measure for patients with congestive heart failure. It is a reliable, predictive tool that tracks how patients are doing if they have weakened heart muscle due to prior heart attacks, heart valve problems, viral infections, or other causes.

The answers patients give to the KCCQ's questions are used to calculate scores in ten scales:
1. Physical Limitation: a measure of how much a patient's condition is hampering his ability to do what he wants to do
2. Symptom Stability: a measure of whether a patient's symptoms are changing over time
3. Symptom Frequency: a measure of how often a patient has symptoms
4. Symptom Burden: a measure of what the impact of these symptoms are on the patient's well-being
5. Total Symptom: a combined measure of the symptom scales
6. Social Limitation: a measure of how much a patient's interpersonal relations are impacted by her condition
7. Self-Efficacy: a measure of how well a patient can manage her care, find answers and help
8. Quality of Life: a measure of the overall impact of a patient's condition on a patient's interpersonal relationships and state of mind
9. Clinical Summary: a combined measure of symptoms and social factors
10. Overall Summary: a combined measure of all the above The term "Spielberg test" refers to the state-trait anxiety inventory for adults developed by Charles D. Spielberg which is well-accepted for measuring different forms of anxiety. The sampler manuals for performing the Spielberg test are published by Mind Gardens, Inc.

The term "Beck Questionnaire Score" refers to a score obtained from the Beck Depression Inventory, a widely used method for measuring depression developed by Aaron Beck. The description of a modern Beck Questionnaire may be found for example in Beck A T, Steer R A, Ball R, Ranieri W (December 1996). "*Comparison of Beck Depression Inventories-IA and-II in psychiatric outpatients*". Journal of personality assessment 67 (3): 588-97, incorporated herein by reference.

The term "in reference to the baseline" with respect to the score obtained from patient questionnaires denotes a comparison to the pre-treatment score of the same patient population.

The present invention provides a pharmaceutical composition for administration to a patient suffering from at least one symptom of a cardiovascular condition associated with a reduced quality of life of the patient, the composition comprising a) an activated-potentiated form of an antibody to the C-terminal fragment of angiotensin II AT1 receptor, and b) an activated-potentiated form of an antibody to endothelial NO-synthase, wherein the administration of the pharmaceutical composition improves quality of life of the patient. As set forth herein above, each of the individual components of the combination is generally known for its own individual medical uses. However, the inventors of the present patent application surprisingly discovered that administration of the combination markedly improves the quality of life of patients with cardiovascular conditions, such as heart failure, asthenia, dystonia, and hypertension.

The pharmaceutical composition in accordance with this aspect of the invention may be in the liquid form or in solid form. Each of the activated potentiated forms of the antibodies included in the pharmaceutical composition is prepared from an initial molecular form of the antibody via a process accepted in homeopathic art. The starting antibodies may be monoclonal, or polyclonal antibodies prepared in accordance with known processes, for example, as described in Immunotechniques, G. Frimel, M., "Meditsyna", 1987, p. 9-33; "Hum. Antibodies. Monoclonal and recombinant antibodies, 30 years after" by Laffly E., Sodoyer R.-2005-Vol. 14.-N 1-2. P. 33-55, both incorporated herein by reference.

Monoclonal antibodies may be obtained, e.g., by means of hybridoma technology. The initial stage of the process includes immunization based on the principles already developed in the course of polyclonal antisera preparation. Further stages of work involve the production of hybrid cells generating clones of antibodies with identical specificity. Their separate isolation is performed using the same methods as in the case of polyclonal antisera preparation.

Polyclonal antibodies may be obtained via active immunization of animals. For this purpose, for example, suitable animals (e.g. rabbits) receive a series of injections of the appropriate antigen, either endothelial NO-synthase or angiotensin II AT1-receptor. The animals' immune system generates corresponding antibodies which are collected from the animals in a known manner. This procedure enables preparation of a monospecific antibody-rich serum. If desired, the serum containing antibodies may be purified, e.g. using affine chromatography, fractionation by salt precipitation, or ion-exchange chromatography. The resulting purified, antibody-enriched serum may be used as a starting material for preparation of the activated-potentiated form of the antibodies. The preferred concentration of the resulting initial solution of antibody in the solvent, preferably, water or a water-ethyl alcohol mixture, ranges from about 0.5 to about 5.0 mg/ml.

The preferred procedure for preparing each component of the combination drug according to the present invention is the use of the mixture of three aqueous-alcohol dilutions of the primary matrix solution of antibodies diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In a preferred embodiment, the starting material for the preparation of the activated potentiated form that comprise the combination of the invention is polyclonal, animal-raised antibody to the corresponding antigen, namely, the C-terminal fragment of angiotensin II AT1 receptor and endothelial NO-synthase. To obtain the activated-potentiated form of polyclonal antibodies to the C-terminal fragment of angiotensin II AT1 receptor, the desired antigen may be injected as immunogen into a laboratory animal, preferably, rabbits. The following sequences of the human angiotensin II AT1 receptor is specifically contemplated as suitable antigens. The use of a whole human angiotensin II AT1 receptor is specifically contemplated:

```
                                                         SEQ ID NO: 1
        Ser Pro Pro Ala Gly Thr Arg His Met Ala Asn Thr Tyr Pro Glu
        1               5                   10                  15

Ala Asn Gly Ile Thr Glu Asn Ser Ile Asn Ile Ile Arg Glu Cys
        16              20                  25                  30

Glu Pro Thr Arg Ser His Met Ser Ala Pro Ile Glu Asn Ser Gly
        31              35                  40                  45

Asn Ala Gly Thr Arg Pro Glu Ser Val Met Ile Leu Asn Ser Ser
        46              50                  55                  60

Thr Glu Asp Gly Ile Lys Arg Ile Gln Asp Asp Cys Pro Lys Ala
        61              65                  70                  75

Gly Arg His Asn Tyr Ile Phe Val Met Ile Pro Thr Leu Tyr Ser
        76              80                  85                  90

Ile Ile Phe Val Val Gly Ile Phe Gly Asn Ser Leu Val Val Ile
        91              95                  100                 105

Val Ile Tyr Phe Tyr Met Lys Leu Lys Thr Val Ala Ser Val Phe
        106             110                 115                 120

Leu Leu Asn Leu Ala Leu Ala Asp Leu Cys Phe Leu Leu Thr Leu
        121             125                 130                 135

Pro Leu Trp Ala Val Tyr Thr Ala Met Glu Tyr Arg Trp Pro Phe
        136             140                 145                 150

Gly Asn Tyr Leu Cys Lys Ile Ala Ser Ala Ser Val Ser Phe Asn
        151             155                 160                 165

Leu Tyr Ala Ser Val Phe Leu Leu Thr Cys Leu Ser Ile Asp Arg
        166             170                 175                 180
```

-continued

```
Tyr Leu Ala Ile Val His Pro Met Lys Ser Arg Leu Arg Arg Thr
181             185                 190                 195

Met Leu Val Ala Lys Val Thr Cys Ile Ile Ile Trp Leu Leu Ala
196             200                 205                 210

Gly Leu Ala Ser Leu Pro Ala Ile Ile His Arg Asn Val Phe Phe
211             215                 220                 225

Ile Glu Asn Thr Asn Ile Thr Val Cys Ala Phe His Tyr Glu Ser
226             230                 235                 240

Gln Asn Ser Thr Leu Pro Ile Gly Leu Gly Leu Thr Lys Asn Ile
241             245                 250                 255

Leu Gly Phe Leu Phe Pro Phe Leu Ile Ile Leu Thr Ser Tyr Thr
256             260                 265                 270

Leu Ile Trp Lys Ala Leu Lys Lys Ala Tyr Glu Ile Gln Lys Asn
271             275                 280                 285

Lys Pro Arg Asn Asp Asp Ile Phe Lys Ile Ile Met Ala Ile Val
286             290                 295                 300

Leu Phe Phe Phe Phe Ser Trp Ile Pro His Gln Ile Phe Thr Phe
301             305                 310                 315

Leu Asp Val Leu Ile Gln Leu Gly Ile Ile Arg Asp Cys Arg Ile
316             320                 325                 330

Ala Asp Ile Val Asp Thr Ala Met Pro Ile Thr Ile Cys Ile Ala
331             335                 340                 345

Tyr Phe Asn Asn Cys Leu Asn Pro Leu Phe Tyr Gly Phe Leu Gly
346             350                 355                 360

Lys Lys Phe Lys Arg Tyr Phe Leu Gln Leu Leu Lys Tyr Ile Pro
361             365                 370                 375

Pro Lys Ala Lys Ser His Ser Asn Leu Ser Thr Lys Met Ser Thr
376             380                 385                 390

Leu Ser Tyr Arg Pro Ser Asp Asn Val Ser Ser Ser Thr Lys Lys
391             395                 400                 405

Pro Ala Pro Cys Phe Glu Val Glu
406             410         413
```

The use of different fragments of C-terminal fragment of human angiotensin II AT1 receptor with as antigen is also contemplated. The suitable sequences for such antigen are as follow:

```
                                                      SEQ ID NO: 2
                                                    Gly
                                                    360

Lys Lys Phe Lys Arg Tyr Phe Leu Gln Leu Leu Lys Tyr Ile Pro
361             365                 370                 375

Pro Lys Ala Lys Ser His Ser Asn Leu Ser Thr Lys Met Ser Thr
376             380                 385                 390

Leu Ser Tyr Arg Pro Ser Asp Asn Val Ser Ser Ser Thr Lys Lys
391             395                 400                 405

Pro Ala Pro Cys Phe Glu Val Glu
406             410         413

SEQ ID NO: 3
                                Gln Leu Leu Lys Tyr Ile Pro
                                369 370                 375

Pro Lys Ala
376     378
```

-continued

```
                                                    SEQ ID NO: 4
                        Ser Asn Leu Ser Thr Lys Met Ser Thr
                        382         385             390

Leu Ser Tyr Arg Pro Ser Asp Asn Val Ser Ser Ser Thr Lys Lys
391         395             400                     405

Pro Ala Pro Cys Phe
406             410
```

The use of the fragments of C-terminal fragment of human angiotensin II AT1 receptor with N-terminal cysteine (Cys) as antigen is also contemplated. The suitable sequence for such antigen is as follow:

```
                                                    SEQ ID NO: 5
                                                Cys Gly
                                                    360

Lys Lys Phe Lys Arg Tyr Phe Leu Gln Leu Leu Lys Tyr Ile Pro
361         365             370                     375

Pro Lys Ala Lys Ser His Ser Asn Leu Ser Thr Lys Met Ser Thr
376         380             385                     390

Leu Ser Tyr Arg Pro Ser Asp Asn Val Ser Ser Ser Thr Lys Lys
391         395             400                     405

Pro Ala Pro Cys Phe Glu Val Glu
406             410     413

SEQ ID NO: 6
                            Cys Gln Leu Leu Lys Tyr Ile Pro
                            369 370                     375

Pro Lys Ala
376     378

SEQ ID NO: 7
                    Cys Ser Asn Leu Ser Thr Lys Met Ser Thr
                        382         385             390

Leu Ser Tyr Arg Pro Ser Asp Asn Val Ser Ser Ser Thr Lys Lys
391         395             400                     405

Pro Ala Pro Cys Phe
406             410
```

The exemplary procedure for preparation of the starting polyclonal antibodies to C-terminal fragment of human angiotensin II AT1 receptor may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections.

To obtain antiserum containing the desired antibodies, the immunized rabbits' blood is collected from rabbits and placed in a 50 ml centrifuge tube. Product clots formed on the tube sides are removed with a wooden spatula, and a rod is placed into the clot in the tube center. The blood is then placed in a refrigerator for one night at the temperature of about 40° C. On the following day, the clot on the spatula is removed, and the remaining liquid is centrifuged for 10 min at 13,000 rpm. Supernatant fluid is the target antiserum. The obtained antiserum is typically yellow. 20% of NaN$_3$ (weight concentration) is added in the antiserum to a final concentration of 0.02% and stored before use in frozen state at the temperature of −20° C. or without NaN$_3$ at the temperature of −70° C. To separate the target antibodies to the C-terminal fragment of angiotensin II AT1 receptor from the antiserum, the following solid phase absorption sequence is suitable:

10 ml of the antiserum of rabbits is diluted twofold with 0.15 M NaCl, after which 6.26 g Na$_2$SO$_4$ is added, mixed and incubated for 12-16 hours at 4° C. The sediment is removed by centrifugation, diluted in 10 ml of phosphate buffer and dialyzed against the same buffer during one night at ambient temperature. After the sediment is removed, the solution is applied to a DEAE-cellulose column balanced by phosphate buffer. The antibody fraction is determined by measuring the optical density of eluate at 280 nm.

The isolated crude antibodies are purified using the affine chromatography method by attaching the obtained antibodies to a C-terminal fragment of angiotensin II AT1 receptor located on the insoluble matrix of the chromatography media, with subsequent elution by concentrated aqueous salt solutions.

The resulting buffer solution is used as the initial solution for the homeopathic dilution process used to prepare the activated potentiated form of the antibodies. The preferred concentration of the initial matrix solution of the antigen-purified polyclonal rabbit antibodies to a C-terminal fragment of angiotensin II AT1 receptor is 0.5-5.0 mg/ml, preferably, 2.0-3.0 mg/ml.

The polyclonal antibodies to endothelial NO-synthase are obtained by a similar methodology using an adjuvant. Preferably, the entire molecule of bovine endothelial NO-synthase is used as immunogen (antigen) for rabbits' immunization:

SEQ.ID. NO. 8

```
Met Gly Asn Leu Lys Ser Val Gly Gln Glu Pro Gly Pro Pro Cys
1               5                   10                  15

Gly Leu Gly Leu Gly Leu Gly Leu Cys Gly Lys Gln Gly
16              20              25              30

Pro Ala Ser Pro Ala Pro Glu Pro Ser Arg Ala Pro Ala Pro Ala
31              35                  40                  45

Thr Pro His Ala Pro Asp His Ser Pro Ala Pro Asn Ser Pro Thr
46              50                  55                  60

Leu Thr Arg Pro Pro Glu Gly Pro Lys Phe Pro Arg Val Lys Asn
61              65                  70                  75

Trp Glu Leu GLys er Ile Thr Tyr Asp Thr Leu Cys Ala Gln Ser
76              80                  85                  90

Gln Gln Asp Gly Pro Cys Thr Pro Arg Cys Cys Leu GLys er Leu
91              95                  100                 105

Val Leu Pro Arg Lys Leu Gln Thr Arg Pro Ser Pro Gly Pro Pro
106             110                 115                 120

Pro Ala Glu Gln Leu Leu Ser Gln Ala Arg Asp Phe Ile Asn Gln
121             125                 130                 135

Tyr Tyr Ser Ser Ile Lys Arg Ser GLys er Gln Ala His Glu Glu
136             140                 145                 150

Arg Leu Gln Glu Val Glu Ala Glu Val Ala Ser Thr Gly Thr Tyr
151             155                 160                 165

His Leu Arg Glu Ser Glu Leu Val Phe Gly Ala Lys Gln Ala Trp
166             170                 175                 180

Arg Asn Ala Pro Arg Cys Val Gly Arg Ile Gln Trp Gly Lys Leu
181             185                 190                 195

Gln Val Phe Asp Ala Arg Asp Cys Ser Ser Ala Gln Glu Met Phe
196             200                 205                 210

Thr Tyr Ile Cys Asn His Ile Lys Tyr Ala Thr Asn Arg Gly Asn
211             215                 220                 225

Leu Arg Ser Ala Ile Thr Val Phe Pro Gln Arg Ala Pro Gly Arg
226             230                 235                 240

Gly Asp Phe Arg Ile Trp Asn Ser Gln Leu Val Arg Tyr Ala Gly
241             245                 250                 255

Tyr Arg Gln Gln Asp GLys er Val Arg Gly Asp Pro Ala Asn Val
256             260                 265                 270

Glu Ile Thr Glu Leu Cys Ile Gln His Gly Trp Thr Pro Gly Asn
271             275                 280                 285

Gly Arg Phe Asp Val Leu Pro Leu Leu Leu Gln Ala Pro Asp Glu
286             290                 295                 300

Ala Pro Glu Leu Phe Val Leu Pro Glu Leu Val Leu Glu Val
301             305                 310                 315

Pro Leu Glu His Pro Thr Leu Glu Trp Phe Ala Ala Leu Gly Leu
316             320                 325                 330

Arg Trp Tyr Ala Leu Pro Ala Val Ser Asn Met Leu Leu Glu Ile
331             335                 340                 345

Gly Gly Leu Glu Phe Ser Ala Ala Pro Phe Ser Gly Trp Tyr Met
346             350                 355                 360
```

-continued

```
Ser Thr Glu Ile Gly Thr Arg Asn Leu Cys Asp Pro His Arg Tyr
361             365                 370                 375

Asn Ile Leu Glu Asp Val Ala Val Cys Met Asp Leu Asp Thr Arg
376             380                 385                 390

Thr Thr Ser Ser Leu Trp Lys Asp Lys Ala Ala Val Glu Ile Asn
391             395                 400                 405

Leu Ala Val Leu His Ser Phe Gln Leu Ala Lys Val Thr Ile Val
406             410                 415                 420

Asp His His Ala Ala Thr Val Ser Phe Met Lys His Leu Asp Asn
421             425                 430                 435

Glu Gln Lys Ala Arg Gly Gly Cys Pro Ala Asp Trp Ala Trp Ile
436             440                 445                 450

Val Pro Pro Ile Ser GLys er Leu Thr Pro Val Phe His Gln Glu
451             455                 460                 465

Met Val Asn Tyr Ile Leu Ser Pro Ala Phe Arg Tyr Gln Pro Asp
466             470                 475                 480

Pro Trp Lys GLy Ser Ala Thr Lys Gly Ala Gly Ile Thr Arg Lys
481             485                 490                 495

Lys Thr Phe Lys Glu Val Ala Asn Ala Val Lys Ile Ser Ala Ser
496             500                 505                 510

Leu Met Gly Thr Leu Met Ala Lys Arg Val Lys Ala Thr Ile Leu
511             515                 510                 525

Tyr Ala Ser Glu Thr Gly Arg Ala Gln Ser Tyr Ala Gln Gln Leu
526             530                 535                 540

Gly Arg Leu Phe Arg Lys Ala Phe Asp Pro Arg Val Leu Cys Met
541             545                 550                 555

Asp Glu Tyr Asp Val Val Ser Leu Glu His Glu Ala Leu Val Leu
556             560                 565                 570

Val Val Thr Ser Thr Phe Gly Asn Gly Asp Pro Pro Glu Asn Gly
571             575                 580                 585

Glu Ser Phe Ala Ala Ala Leu Met Glu Met Ser Gly Pro Tyr Asn
586             590                 595                 600

Ser Ser Pro Arg Pro Glu Gln His Lys Ser Tyr Lys Ile Arg Phe
601             605                 610                 615

Asn Ser Val Ser Cys Ser Asp Pro Leu Val Ser Ser Trp Arg Arg
616             620                 625                 630

Lys Arg Lys Glu Ser Ser Asn Thr Asp Ser Ala Gly Ala Leu Gly
631             635                 640                 645

Thr Leu Arg Phe Cys Val Phe Gly Leu GLy Ser Arg Ala Tyr Pro
646             650                 655                 660

His Phe Cys Ala Phe Ala Arg Ala Val Asp Thr Arg Leu Glu Glu
661             665                 670                 675

Leu Gly Gly Glu Arg Leu Leu Gln Leu Gly Gln Gly Asp Glu Leu
676             680                 685                 690

Cys Gly Gln Glu Glu Ala Phe Arg Gly Trp Ala Lys Ala Ala Phe
691             695                 700                 705

Gln Ala Ser Cys Glu Thr Phe Cys Val Gly Glu Glu Ala Lys Ala
706             710                 715                 720

Ala Ala Gln Asp Ile Phe Ser Pro Lys Arg Ser Trp Lys Arg Gln
721             725                 730                 735

Arg Tyr Arg Leu Ser Thr Gln Ala Glu Gly Leu Gln Leu Leu Pro
736             740                 745                 750

Gly Leu Ile His Val His Arg Arg Lys Met Phe Gln Ala Thr Val
751             755                 760                 765
```

-continued

```
Leu Ser Val Glu Asn Leu Gln Ser Ser Lys Ser Thr Arg Ala Thr
766                 770                 775                 780

Ile Leu Val Arg Leu Asp Thr Ala Gly Gln Glu Gly Leu Gln Tyr
781                 785                 790                 795

Gln Pro Gly Asp His Ile Gly Ile Cys Pro Pro Asn Arg Pro Gly
796                 800                 805                 810

Leu Val Glu Ala Leu Leu Ser Arg Val Glu Asp Pro Pro Pro
811                 815                 820                 825

Thr Glu Ser Val Ala Val Glu Gln Leu Glu Lys GLys er Pro Gly
826                 830                 835                 840

Gly Pro Pro Pro Ser Trp Val Arg Asp Pro Arg Leu Pro Pro Cys
841                 845                 850                 855

Thr Leu Arg Gln Ala Leu Thr Phe Phe Leu Asp Ile Thr Ser Pro
856                 860                 865                 870

Pro Ser Pro Arg Leu Leu Arg Leu Leu Ser Thr Leu Ala Glu Glu
871                 875                 880                 885

Pro Ser Glu Gln Gln Glu Leu Glu Thr Leu Ser Gln Asp Pro Arg
886                 890                 895                 900

Arg Tyr Glu Glu Trp Lys Trp Phe Arg Cys Pro Thr Leu Leu Glu
901                 905                 910                 915

Val Leu Glu Gln Phe Pro Ser Val Ala Leu Pro Ala Pro Leu Leu
916                 920                 925                 930

Leu Thr Gln Leu Pro Leu Leu Gln Pro Arg Tyr Tyr Ser Val Ser
931                 935                 940                 945

Ser Ala Pro Asn Ala His Pro Gly Glu Val His Leu Thr Val Ala
946                 950                 955                 960

Val Leu Ala Tyr Arg Thr Gln Asp Gly Leu Gly Pro Leu His Tyr
961                 965                 970                 975

Gly Val Cys Ser Thr Trp Leu Ser Gln Leu Lys Thr Gly Asp Pro
976                 980                 985                 990

Val Pro Cys Phe Ile Arg Gly Ala Pro Ser Phe Arg Leu Pro Pro
991                 995                 1000                1005

Asp Pro Tyr Val Pro Cys Ile Leu Val Gly Pro Gly Thr Gly Ile
1006                1010                1015                1020

Ala Pro Phe Arg Gly Phe Trp Gln Glu Arg Leu His Asp Ile Glu
1021                1025                1030                1035

Ser Lys Gly Leu Gln Pro Ala Pro Met Thr Leu Val Phe Gly Cys
1036                1040                1045                1050

Arg Cys Ser Gln Leu Asp His Leu Tyr Arg Asp Glu Val Gln Asp
1051                1055                1060                1065

Ala Gln Glu Arg Gly Val Phe Gly Arg Val Leu Thr Ala Phe Ser
1066                1070                1075                1080

Arg Glu Pro Asp Ser Pro Lys Thr Tyr Val Gln Asp Ile Leu Arg
1081                1085                1090                1095

Thr Glu Leu Ala Ala Glu Val His Arg Val Leu Cys Leu Glu Arg
1096                1100                1105                1110

Gly His Met Phe Val Cys Gly Asp Val Thr Met Ala Thr Ser Val
1111                1115                1120                1125

Leu Gln Thr Val Gln Arg Ile Leu Ala Thr Glu Gly Asp Met Glu
1126                1130                1135                1140

Leu Asp Glu Ala Gly Asp Val Ile Gly Val Leu Arg Asp Gln Gln
1141                1145                1150                1155

Arg Tyr His Glu Asp Ile Phe Gly Leu Thr Leu Arg Thr Gln Glu
1156                1160                1165                1170
```

-continued

```
Val Thr Ser Arg Ile Arg Thr Gln Ser Phe Ser Leu Gln Glu Arg
1171          1175              1180             1185

His Leu Arg Gly Ala Val Pro Trp Ala Phe Asp Pro Pro Gly Pro
1186          1190              1195             1200

Asp Thr Pro Gly Pro
1201          1205
```

Polyclonal antibodies to endothelial NO synthase may be obtained using the whole molecule of human endothelial NO synthase of the following sequence:

```
                                                          SEQ ID NO: 9
Met Gly Asn Leu Lys Ser Val Ala Gln Glu Pro Gly Pro Pro Cys
1             5                   10                  15

Gly Leu Gly Leu Gly Leu Gly Leu Cys Gly Lys Gln Gly
16            20                  25                  30

Pro Ala Thr Pro Ala Pro Glu Pro Ser Arg Ala Pro Ala Ser Leu
31            35                  40                  45

Leu Pro Pro Ala Pro Glu His Ser Pro Ser Ser Pro Leu Thr
46            50                  55                  60

Gln Pro Pro Glu Gly Pro Lys Phe Pro Arg Val Lys Asn Trp Glu
61            65                  70                  75

Val GLys er Ile Thr Tyr Asp Thr Leu Ser Ala Gln Ala Gln Gln
76            80                  85                  90

Asp Gly Pro Cys Thr Pro Arg Arg Cys Leu GLys er Leu Val Phe
91            95                  100                 105

Pro Arg Lys Leu Gln Gly Arg Pro Ser Pro Gly Pro Pro Ala Pro
106           110                 115                 120

Glu Gln Leu Leu Ser Gln Ala Arg Asp Phe Ile Asn Gln Tyr Tyr
121           125                 130                 135

Ser Ser Ile Lys Arg Ser GLys er Gln Ala His Glu Gln Arg Leu
136           140                 145                 150

Gln Glu Val Glu Ala Glu Val Ala Ala Thr Gly Thr Tyr Gln Leu
151           155                 160                 165

Arg Glu Ser Glu Leu Val Phe Gly Ala Lys Gln Ala Trp Arg Asn
166           170                 175                 180

Ala Pro Arg Cys Val Gly Arg Ile Gln Trp Gly Lys Leu Gln Val
181           185                 190                 195

Phe Asp Ala Arg Asp Cys Arg Ser Ala Gln Glu Met Phe Thr Tyr
196           200                 205                 210

Ile Cys Asn His Ile Lys Tyr Ala Thr Asn Arg Gly Asn Leu Arg
211           215                 220                 225

Ser Ala Ile Thr Val Phe Pro Gln Arg Cys Pro Gly Arg Gly Asp
226           230                 235                 240

Phe Arg Ile Trp Asn Ser Gln Leu Val Arg Tyr Ala Gly Tyr Arg
241           245                 250                 255

Gln Gln Asp GLy Ser Val Arg Gly Asp Pro Ala Asn Val Glu Ile
256           260                 265                 270

Thr Glu Leu Cys Ile Gln His Gly Trp Thr Pro Gly Asn Gly Arg
271           275                 280                 285

Phe Asp Val Leu Pro Leu Leu Leu Gln Ala Pro Asp Glu Pro Pro
286           290                 295                 300

Glu Leu Phe Leu Leu Pro Pro Glu Leu Val Leu Glu Val Pro Leu
301           305                 310                 315
```

```
Glu His Pro Thr Leu Glu Trp Phe Ala Ala Leu Gly Leu Arg Trp
316                 320                 325                 330

Tyr Ala Leu Pro Ala Val Ser Asn Met Leu Leu Glu Ile Gly Gly
331                 335                 340                 345

Leu Glu Phe Pro Ala Ala Pro Phe Ser Gly Trp Tyr Met Ser Thr
346                 350                 355                 360

Glu Ile Gly Thr Arg Asn Leu Cys Asp Pro His Arg Tyr Asn Ile
361                 365                 370                 375

Leu Glu Asp Val Ala Val Cys Met Asp Leu Asp Thr Arg Thr Thr
376                 380                 385                 390

Ser Ser Leu Trp Lys Asp Lys Ala Ala Val Glu Ile Asn Val Ala
391                 395                 400                 405

Val Leu His Ser Tyr Gln Leu Ala Lys Val Thr Ile Val Asp His
406                 410                 415                 420

His Ala Ala Thr Ala Ser Phe Met Lys His Leu Glu Asn Glu Gln
421                 425                 430                 435

Lys Ala Arg Gly Gly Cys Pro Ala Asp Trp Ala Trp Ile Val Pro
436                 440                 445                 450

Pro Ile Ser GLys er Leu Thr Pro Val Phe His Gln Glu Met Val
451                 455                 460                 465

Asn Tyr Phe Leu Ser Pro Ala Phe Arg Tyr Gln Pro Asp Pro Trp
466                 470                 475                 480

Lys GLys er Ala Ala Lys Gly Thr Gly Ile Thr Arg Lys Lys Thr
481                 485                 490                 495

Phe Lys Glu Val Ala Asn Ala Val Lys Ile Ser Ala Ser Leu Met
496                 500                 505                 510

Gly Thr Val Met Ala Lys Arg Val Lys Ala Thr Ile Leu Tyr Gly
511                 515                 510                 525

Ser Glu Thr Gly Arg Ala Gln Ser Tyr Ala Gln Gln Leu Gly Arg
526                 530                 535                 540

Leu Phe Arg Lys Ala Phe Asp Pro Arg Val Leu Cys Met Asp Glu
541                 545                 550                 555

Tyr Asp Val Val Ser Leu Glu His Glu Thr Leu Val Leu Val Val
556                 560                 565                 570

Thr Ser Thr Phe Gly Asn Gly Asp Pro Pro Glu Asn Gly Glu Ser
571                 575                 580                 585

Phe Ala Ala Ala Leu Met Glu Met Ser Gly Pro Tyr Asn Ser Ser
586                 590                 595                 600

Pro Arg Pro Glu Gln His Lys Ser Tyr Lys Ile Arg Phe Asn Ser
601                 605                 610                 615

Ile Ser Cys Ser Asp Pro Leu Val Ser Trp Arg Arg Lys Arg
616                 620                 625                 630

Lys Glu Ser Ser Asn Thr Asp Ser Ala Gly Ala Leu Gly Thr Leu
631                 635                 640                 645

Arg Phe Cys Val Phe Gly Leu GLys er Arg Ala Tyr Pro His Phe
646                 650                 655                 660

Cys Ala Phe Ala Arg Ala Val Asp Thr Arg Leu Glu Glu Leu Gly
661                 665                 670                 675

Gly Glu Arg Leu Leu Gln Leu Gly Gln Gly Asp Glu Leu Cys Gly
676                 680                 685                 690

Gln Glu Glu Ala Phe Arg Gly Trp Ala Gln Ala Ala Phe Gln Ala
691                 695                 700                 705

Ala Cys Glu Thr Phe Cys Val Gly Glu Asp Ala Lys Ala Ala Ala
706                 710                 715                 720
```

-continued

```
Arg Asp Ile Phe Ser Pro Lys Arg Ser Trp Lys Arg Gln Arg Tyr
721                 725                 730                 735

Arg Leu Ser Ala Gln Ala Glu Gly Leu Gln Leu Leu Pro Gly Leu
736                 740                 745                 750

Ile His Val His Arg Arg Lys Met Phe Gln Ala Thr Ile Arg Ser
751                 755                 760                 765

Val Glu Asn Leu Gln Ser Ser Lys Ser Thr Arg Ala Thr Ile Leu
766                 770                 775                 780

Val Arg Leu Asp Thr Gly Gly Gln Glu Gly Leu Gln Tyr Gln Pro
781                 785                 790                 795

Gly Asp His Ile Gly Val Cys Pro Pro Asn Arg Pro Gly Leu Val
796                 800                 805                 810

Glu Ala Leu Leu Ser Arg Val Glu Asp Pro Pro Ala Pro Thr Glu
811                 815                 820                 825

Pro Val Ala Val Glu Gln Leu Glu Lys Gly Ser Pro Gly Gly Pro
826                 830                 835                 840

Pro Pro Gly Trp Val Arg Asp Pro Arg Leu Pro Pro Cys Thr Leu
841                 845                 850                 855

Arg Gln Ala Leu Thr Phe Phe Leu Asp Ile Thr Ser Pro Pro Ser
856                 860                 865                 870

Pro Gln Leu Leu Arg Leu Leu Ser Thr Leu Ala Glu Glu Pro Arg
871                 875                 880                 885

Glu Gln Gln Glu Leu Glu Ala Leu Ser Gln Asp Pro Arg Arg Tyr
886                 890                 895                 900

Glu Glu Trp Lys Trp Phe Arg Cys Pro Thr Leu Leu Glu Val Leu
901                 905                 910                 915

Glu Gln Phe Pro Ser Val Ala Leu Pro Ala Pro Leu Leu Leu Thr
916                 920                 925                 930

Gln Leu Pro Leu Leu Gln Pro Arg Tyr Tyr Ser Val Ser Ser Ala
931                 935                 940                 945

Pro Ser Thr His Pro Gly Glu Ile His Leu Thr Val Ala Val Leu
946                 950                 955                 960

Ala Tyr Arg Thr Gln Asp Gly Leu Gly Pro Leu His Tyr Gly Val
961                 965                 970                 975

Cys Ser Thr Trp Leu Ser Gln Leu Lys Pro Gly Asp Pro Val Pro
976                 980                 985                 990

Cys Phe Ile Arg Gly Ala Pro Ser Phe Arg Leu Pro Pro Asp Pro
991                 995                 1000                1005

Ser Leu Pro Cys Ile Leu Val Gly Pro Gly Thr Gly Ile Ala Pro
1006                1010                1015                1020

Phe Arg Gly Phe Trp Gln Glu Arg Leu His Asp Ile Glu Ser Lys
1021                1025                1030                1035

Gly Leu Gln Pro Thr Pro Met Thr Leu Val Phe Gly Cys Arg Cys
1036                1040                1045                1050

Ser Gln Leu Asp His Leu Tyr Arg Asp Glu Val Gln Asn Ala Gln
1051                1055                1060                1065

Gln Arg Gly Val Phe Gly Arg Val Leu Thr Ala Phe Ser Arg Glu
1066                1070                1075                1080

Pro Asp Asn Pro Lys Thr Tyr Val Gln Asp Ile Leu Arg Thr Glu
1081                1085                1090                1095

Leu Ala Ala Glu Val His Arg Val Leu Cys Leu Glu Arg Gly His
1096                1100                1105                1110

Met Phe Val Cys Gly Asp Val Thr Met Ala Thr Asn Val Leu Gln
1111                1115                1120                1125
```

```
                            -continued
Thr Val Gln Arg Ile Leu Ala Thr Glu Gly Asp Met Glu Leu Asp
1126        1130            1135            1140

Glu Ala Gly Asp Val Ile Gly Val Leu Arg Asp Gln Gln Arg Tyr
1141        1145            1150            1155

His Glu Asp Ile Phe Gly Leu Thr Leu Arg Thr Gln Glu Val Thr
1156        1160            1165            1170

Ser Arg Ile Arg Thr Gln Ser Phe Ser Leu Gln Glu Arg Gln Leu
1171        1175            1180            1185

Arg Gly Ala Val Pro Trp Ala Phe Asp Pro Pro Gly Ser Asp Thr
1186        1190            1195            1200

Asn Ser Pro
1201    1203
```

To obtain polyclonal antibodies to endothelial NO synthase, it is also possible to use a fragment of endothelial NO synthase, selected, for example, from the following sequences:

```
                                        SEQ ID NO: 10
Pro Trp Ala Phe
1192        1195

SEQ ID NO: 11
Gly Ala Val Pro
1189        1192

SEQ ID NO: 12
                                        Arg
                                        1185

His Leu Arg Gly Ala Val Pro Trp Ala Phe Asp Pro Pro Gly Pro
1186        1190            1195            1200

Asp Thr Pro Gly Pro
1201        1205

SEQ. ID. NO: 13
                        Ala Phe Asp Pro Pro Gly Pro
                        11941195            1200

Asp Thr Pro Gly Pro
1201        1205

SEQ. NO. 14
His Leu Arg Gly Ala Val Pro Trp Ala Phe Asp
1186        1190            11951196

SEQ ID NO: 15
His Leu Arg Gly Ala Val Pro Trp Ala Phe Asp Pro Pro Gly Pro
1186        1190            1195            1200

Asp Thr Pro Gly Pro
1201        1205
```

The activated potentiated form of each component of the combination may be prepared from an initial solution by homeopathic potentization, preferably using the method of proportional concentration decrease by serial dilution of 1 part of each preceding solution (beginning with the initial solution) in 9 parts (for decimal dilution), or in 99 parts (for centesimal dilution), or in 999 parts (for millesimal dilution) of a neutral solvent, starting with a concentration of the initial solution of antibody in the solvent, preferably, water or a water-ethyl alcohol mixture, in the range from about 0.5 to about 5.0 mg/ml, coupled with external impact. Preferably, the external impact involves multiple vertical shaking (dynamization) of each dilution. Preferably, separate containers are used for each subsequent dilution up to the required potency level, or the dilution factor. This method is well-accepted in the homeopathic art. See, e.g. V. Schwabe "Homeopathic medicines", M., 1967, p. 14-29, incorporated herein by reference for the purpose stated.

For example, to prepare a 12-centesimal dilution (denoted C12), one part of the initial matrix solution of antibodies, for example, to C-terminal fragment of angiotensin II AT1 receptor with the concentration of 3.0 mg/m$^1$ is diluted in 99 parts of neutral aqueous or aqueous-alcohol solvent (preferably, 15%-ethyl alcohol) and then vertically shaked many times (10 and more) to create the 1st centesimal dilution (denoted as C1). The 2nd centesimal dilution (C2) is prepared from the 1st centesimal dilution C1. This procedure is repeated 11 times to prepare the 12th centesimal dilution C12. Thus, the 12th centesimal dilution C12 represents a solution obtained by 12 serial dilutions of one part of the initial matrix solution of antibodies to C-terminal fragment of angiotensin II AT1 receptor with the concentration of 3.0 mg/ml in 99 parts of a neutral solvent in different containers, which is equivalent to the centesimal homeopathic dilution C12. Similar procedures with the relevant dilution factor are performed to obtain dilutions C30 and C 200. The intermediate dilutions may be tested in a desired biological model to check activity. The preferred activated potentiated forms for both antibodies comprising the combination of the invention are a mixture of C12, C30, and C200 dilutions. When using the mixture of various homeopathic dilutions (primarily centesimal) of the active substance as biologically active liquid component, each component of the composition (e.g., C12, C30, C200) is prepared separately according to the above-described procedure until the next-to-last dilution is obtained (e.g., until C11, C29, and C199 respectively), and then one part of each component is added in one container according to the mixture composition and mixed with the required quantity of the solvent (e.g. with 97 parts for centesimal dilution).

It is possible to use the active substance as mixture of various homeopathic dilutions, e.g. decimal and/or centesimal (D20, C30, C100 or C12, C30, C50 etc.), the efficiency of which is determined experimentally by testing the dilution in a suitable biological model, for example, in models described in the examples herein.

In the course of potentiation and concentration decrease, the vertical shaking may be substituted for external exposure to ultrasound, electromagnetic field or any similar external impact procedure accepted in the homeopathic art.

Preferably, the pharmaceutical composition of the invention may be in the form of a liquid or in the solid unit dosage form. The preferred liquid form of the pharmaceutical composition is a mixture, preferably at a 1:1 ratio of the activated potentiated form of antibodies to a C-terminal fragment of angiotensin II AT1 receptor and the activated potentiated form of antibodies to endothelial NO-synthase. The preferred liquid carrier is water or a water-ethyl alcohol mixture.

The solid unit dosage form of the pharmaceutical composition of the invention may be prepared by impregnating a solid, pharmaceutically acceptable carrier with the mixture of the activated potentiated form aqueous or aqueous-alcohol solutions of active components which are mixed, primarily in 1:1 ratio and used in liquid dosage form. Alternatively, the carrier may be impregnated consecutively with each requisite dilution. Both orders of impregnation are acceptable.

Preferably, the pharmaceutical composition in the solid unit dosage form is prepared from granules of the pharmaceutically acceptable carrier which were previously saturated with the aqueous or aqueous-alcoholic dilutions of the activated potentiated form of antibodies to a C-terminal fragment of angiotensin II AT1 receptor and the activated potentiated form of antibodies to endothelial NO-synthase. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono- olygo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc), including lubricants, disintegrants, binders and coloring agents. The preferred carriers are lactose and isomalt. The pharmaceutical dosage form may further include standard pharmaceutical excipients, for example, microcrystalline cellulose, magnesium stearate and citric acid.

The example of preparation of the solid unit dosage form is set forth below. To prepare the solid oral form, 100-300 µm granules of lactose are impregnated with aqueous or aqueous-alcoholic solutions of the activated-potentiated form of antibodies to C-terminal fragment of angiotensin II AT1 receptor and the activated-potentiated form of antibodies to endothelial NO-synthase in the ratio of 1 kg of antibody solution to 5 or 10 kg of lactose (1:5-1:10). To effect impregnation, the lactose granules are exposed to saturation irrigation in the fluidized boiling bed in the boiling bed plant (e.g. "Hüttlin Pilotlab" by Hüttlin GmbH) with subsequent drying via heated air flow at a temperature below 40° C. The estimated quantity of the dried granules (10 to 34 weight parts) saturated with the activated potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch-XL 400 tablet press) to form 150 to 500 mg round pills, preferably, 300 mg. After tableting, 300 mg pills are obtained that are saturated with aqueous-alcohol solution (3.0-6.0 mg/pill) of the combination of the activated-potentiated form of antibodies to C-terminal fragment of angiotensin II AT1 receptor and the activated potentiated form of antibodies to endothelial NO-synthase. Each component of the combination used to impregnate the carrier is in the form of a mixture of centesimal homeopathic dilutions, preferably, C12, C30 and C200. While the invention is not limited to any specific theory, it is believed that the activated potentiated form of the antibodies described herein do not contain the molecular form of the antibody in an amount sufficient to have biological activity attributed to such molecular form. The biological activity of the combination drug (combination pharmaceutical composition) of the invention is amply demonstrated in the appended examples.

The combination pharmaceutical composition of the invention may be used for administration to patients having any cardiovascular condition specifically for the purpose of improving the quality of life of such patients. Such use is particularly advantageous because the side effect profile of the combination of the invention is highly favorable. Patients with cardiovascular conditions suffer from decreased quality of life due to their symptoms and decrease in their ability to engage in routine tasks, such as walking, moving items in their environment, depression, and anxiety. As shown in the appended examples, the administration of the combination drug of the invention to such patients improves their overall quality of life, ability to walk, decreases anxiety and depression associated specifically with their primary condition of the cardiovascular system.

The population of patients suffering from cardiovascular conditions, such as, for example, chronic heart failure, asthenia, dystonia, hypertension, and others, is routinely prescribed a variety of medications to treat their conditions. The use of the combination drug of the invention with such additional therapeutic agents to improve the quality of life, to treat chronic heart failure, dystonia, asthenia, and hypertension is specifically contemplated. Non-limiting examples of suitable additional therapeutic agents include:

ACE inhibitors, including combined ones (Enap, Enalapril, Capoten, Renitec, Prestarium (Berlipril, Diroton, Capoten, Quadropril, Monopril, Renitec, Prestarium, Noliprel-Forte, Enap-N));

diuretics (Furosemide, Veroshpiron, Hypothiazid, Arifon Retard, Indapamide, Hypothiazid, Diuver, Indap, Indapamide);

β-adrenergic blockers (Egilok, Atenolol, Concor, Betaloc ZOK);

nitrates (Dilasidom, Kardiket, Kardiket-Retord, Mitrolinate, MonoMak, Monocinque, Nitroglycerin, Nitrosorbid, Olicard, Pectrol, Sydnopharm);

cardiac glycosides (Digoxin);

calcium antagonists (Normodipin, Cordaflex, Amlovas, Amlodipine, Amlovas, Amlotop, Cardilopin, Cordaflex, Cordipin XL);

hypolipidemic agents (Vasilip, Liprimar, Liptonorm, Simvahexyl, Simvastol, Simvacard, Simgal, Tulip);

antiaggregants (Acetylsalicylic acid, CardiASK, Cardiomagnyl, Thrombo ASS);

antihypoxants (Preductal MB, Preductal, Trimectal);

anticoagulants (Warfarin).

Preferably, for the purpose of improving the quality of life, the combination drug of the invention is administered from once daily to four times daily, each administration including one or two combination unit dosage forms.

It is known that a variety of cardiovascular conditions is accompanied with anxiety and/or depression in the relevant population of patients. The administration of the combination drug described herein to such patients results in a statistically significant improvement in the levels of anxiety and/or depression as measured by the well-accepted tests described herein and exemplified in the examples.

The combination pharmaceutical composition of the invention is also useful for treating chronic heart failure, primarily at the $1^{st}$ and $2^{nd}$ stages of the disease. It has been demonstrated experimentally that the administration of the combination pharmaceutical composition of the invention to patients that suffer from chronic heart failure leads to statistically significant improvement in rigidity parameters of carotid radial artery segments and carotid femoral artery segments. The combination of the invention provides an unexpected synergistic therapeutic effect and enhanced influence on vascular remodeling and endothelium dysfunction that is significant for the process and progression of treatment of chronic heart failure, as also on the improvement of the patients' life quality, on morphological parameters of the heart and tolerance to physical exercise, which is confirmed by clinical trials.

The administration of the combination pharmaceutical composition for treatment of patients with chronic heart failure improves the life quality parameters evaluated by such criteria as depression, anxiety, walking duration, increased tolerance to physical exercise, etc. The patients that suffer from chronic heart failure also often suffer from associated anxiety and/or depression. The administration of the combination pharmaceutical composition to patients that suffer from chronic heart failure leads to a statistically significant reduction in anxiety and depression associated with their primary condition. It has been demonstrated experimentally that the administration of the combination to patients with chronic heart failure leads to statistically significant improvement in The Minnesota Living with Heart Failure questionnaire Score, Kansas City Cardiomyopathy Questionnaire Total Score, HADS Total Score, and 6-minute walking test.

The population of patients suffering from chronic heart failure is routinely prescribed a variety of medications to treat their condition. The use of the combination drug of the invention with such additional therapeutic agents to improve the quality of life, to treat chronic heart failure, dystonia, asthenia, and hypertension is specifically contemplated. Non-limiting examples of suitable additional therapeutic agents include ACE inhibitors, including combined ones (Enap, Enalapril, Capoten, Renitec, Prestarium (Berlipril, Diroton, Capoten, Quadropril, Monopril, Renitec, Prestarium, Noliprel-Forte, Enap-N));

diuretics (Furosemide, Veroshpiron, Hypothiazid, Arifon Retard, Indapamide, Hypothiazid, Diuver, Indap, Indapamide);

β-adrenergic blockers (Egilok, Atenolol, Concor, Betaloc ZOK);

nitrates (Dilasidom, Kardiket, Kardiket-Retord, Mitrolinate, MonoMak, Monocinque, Nitroglycerin, Nitrosorbid, Olicard, Pectrol, Sydnopharm);

cardiac glycosides (Digoxin);

calcium antagonists (Normodipin, Cordaflex, Amlovas, Amlodipine, Amlovas, Amlotop, Cardilopin, Cordaflex, Cordipin XL);

hypolipidemic agents (Vasilip, Liprimar, Liptonorm, Simvahexyl, Simvastol, Simvacard, Simgal, Tulip);

antiaggregants (Acetylsalicylic acid, CardiASK, Cardiomagnyl, Thrombo ASS);

antihypoxants (Preductal MB, Preductal, Trimectal);

anticoagulants (Warfarin).

Particularly preferred are those additional therapeutic agents that are used in the medical art to treat chronic heart failure.

Preferably, for the purpose of treating chronic heart failure, the combination drug of the invention is administered from once daily to four times daily, each administration including one or two combination unit dosage forms. Each of the specific administration regiments within the described range is separately and specifically contemplated.

Separate administration of two independently prepared unit dosage forms, each containing one of the activated potentiated forms of antibodies of the combination is also contemplated.

The combination pharmaceutical composition of the invention is also useful for treating patients that suffer from asthenia and/or vegetative-vascular dystonia. It has been demonstrated experimentally that the administration of the combination pharmaceutical composition of the invention to patients that suffer from asthenia and/or vegetative-vascular dystonia leads to statistically significant improvement in rigidity parameters of carotid radial artery segments and carotid femoral artery segments. The combination pharmaceutical composition of the invention provides an unexpected synergistic therapeutic effect and enhanced influence on vascular remodeling and endothelium dysfunction that is significant for the process and progression of treatment of asthenia and/or vegetative-vascular dystonia, as also on the improvement of the patients' life quality, on morphological parameters of the heart and tolerance to physical exercise, which is confirmed by clinical trials.

The administration of the combination pharmaceutical composition for treatment of patients with asthenia and/or vegetative-vascular dystonia improves the life quality parameters evaluated by such criteria as depression, anxiety, walking duration, increased tolerance to physical exercise, etc. The patients that suffer from asthenia and/or vegetative-vascular dystonia also often suffer from associated anxiety and/or depression. The administration of the combination pharmaceutical composition to patients that suffer from asthenia and/or vegetative-vascular dystonia leads to a statistically significant reduction in anxiety and depression associated with their primary condition. It has been demonstrated experimentally that the administration of the combination pharmaceutical composition to patients with asthenia and/or vegetative-vascular dystonia leads to statistically significant reduction in MFI-20 scale score for mental asthenia and improvements in trait anxiety as measured by the Spielberg test.

The population of patients suffering from asthenia and/or vegetative-vascular dystonia is routinely prescribed a variety of medications to treat their condition. The use of the combination pharmaceutical composition of the invention with such additional therapeutic agents to improve the quality of life, to treat dystonia and asthenia is specifically contemplated. Non-limiting examples of suitable additional therapeutic agents include

- ACE inhibitors, including combined ones (Enap, Enalapril, Capoten, Renitec, Prestarium (Berlipril, Diroton, Capoten, Quadropril, Monopril, Renitec, Prestarium, Noliprel-Forte, Enap-N));
- diuretics (Furosemide, Veroshpiron, Hypothiazid, Arifon Retard, Indapamide, Hypothiazid, Diuver, Indap, Indapamide);
- β-adrenergic blockers (Egilok, Atenolol, Concor, Betaloc ZOK);
- nitrates (Dilasidom, Kardiket, Kardiket-Retord, Mitrolinate, MonoMak, Monocinque, Nitroglycerin, Nitrosorbid, Olicard, Pectrol, Sydnopharm);
- cardiac glycosides (Digoxin);
- calcium antagonists (Normodipin, Cordaflex, Amlovas, Amlodipine, Amlovas, Amlotop, Cardilopin, Cordaflex, Cordipin XL);
- hypolipidemic agents (Vasilip, Liprimar, Liptonorm, Simvahexyl, Simvastol, Simvacard, Simgal, Tulip);
- antiaggregants (Acetylsalicylic acid, CardiASK, Cardiomagnyl, Thrombo ASS);
- antihypoxants (Preductal MB, Preductal, Trimectal);
- anticoagulants (Warfarin).

Particularly preferred are those additional therapeutic agents that are used in the medical art to treat asthenia and/or vegetative-vascular dystonia.

Preferably, for the purpose of treating asthenia and/or vegetative-vascular dystonia, the combination pharmaceutical composition of the invention is administered from once daily to four times daily, each administration including one or two combination unit dosage forms. Each of the specific administration regimens within the described range is separately and specifically contemplated. Separate administration of two independently prepared unit dosage forms, each containing one of the activated potentiated forms of antibodies of the combination drug is also contemplated.

The combination pharmaceutical composition of the invention is also useful for treating hypertension. It has been demonstrated experimentally that the administration of the combination pharmaceutical composition leads to statistically significant reduction in systolic blood pressure. The population of patients suffering from hypertension is routinely prescribed a variety of medications to treat their condition. The use of the combination pharmaceutical composition of the invention with such additional therapeutic agents to treat hypertension is specifically contemplated. Non-limiting examples of suitable additional therapeutic agents include

- ACE inhibitors, including combined ones (Enap, Enalapril, Capoten, Renitec, Prestarium (Berlipril, Diroton, Capoten, Quadropril, Monopril, Renitec, Prestarium, Noliprel-Forte, Enap-N));
- diuretics (Furosemide, Veroshpiron, Hypothiazid, Arifon Retard, Indapamide, Hypothiazid, Diuver, Indap, Indapamide);
- β-adrenergic blockers (Egilok, Atenolol, Concor, Betaloc ZOK);
- nitrates (Dilasidom, Kardiket, Kardiket-Retord, Mitrolinate, MonoMak, Monocinque, Nitroglycerin, Nitrosorbid, Olicard, Pectrol, Sydnopharm);
- cardiac glycosides (Digoxin);
- calcium antagonists (Normodipin, Cordaflex, Amlovas, Amlodipine, Amlovas, Amlotop, Cardilopin, Cordaflex, Cordipin XL);
- hypolipidemic agents (Vasilip, Liprimar, Liptonorm, Simvahexyl, Simvastol, Simvacard, Simgal, Tulip);
- antiaggregants (Acetylsalicylic acid, CardiASK, Cardiomagnyl, Thrombo ASS);
- antihypoxants (Preductal MB, Preductal, Trimectal);
- anticoagulants (Warfarin).

Particularly preferred are those additional therapeutic agents that are used in the medical art to treat hypertension.

Preferably, for the purpose of treating hypertension, the combination pharmaceutical composition of the invention is administered from once daily to four times daily, each administration including one or two combination unit dosage forms. Each of the specific administration regimens within the described range is separately and specifically contemplated. Separate administration of two independently prepared unit dosage forms, each containing one of the activated potentiated forms of antibodies of the combination pharmaceutical composition is also contemplated.

The invention is further illustrated with reference to the appended non-limiting examples.

EXAMPLES

Example 1

Study of the efficacy of the combined drug based on ultra-low doses (ULD), i.e. the activated-potentiated solutions as described above, of antibodies to a C-terminal fragment of angiotensin II AT1 receptor and antibodies to endothelial NO synthase (mixture of homeopathic dilutions C12, C30 and C200) in chronic heart failure (CHF) was conducted in 75 female Wistar rats (4-5 months old, weighing 220-250 g).

For chronic heart failure modeling all rats were receiving isadrine (isoproterenol hydrochloride, Sigma, Germany) 80 mg/kg twice with 24-hour interval. Animals (15 per group) were receiving the following drugs by gastric gavage: group 1—7.5 mL/kg of ULD of antibodies against a C-terminal fragment of angiotensin II AT1 receptor (mixture of homeopathic dilutions C12, C30 and C200), group 2—7.5 mL/kg of ULD of anti-endothelial NO synthase antibodies (mixture of homeopathic dilutions C12, C30 and C200), group 3—15 mL/kg of combined drug (mixture of homeopathic dilutions C12, C30 and C200), group 4—7.5 mL/kg (dose of 10 mg/kg) of losartan as a comparator, group 5 (control)—7.5 mL/kg of distilled water.

The drug efficacy was assessed on Days 7, 14, 28 after repeated isadrine administration based on electrocardiogram and rheogram data, as well as the results of exercise tolerance test (swimming with weight load of 15% of the body weight at a water temperature of 24° C.).

In 7 days following the second isadrine injection animals from all experimental groups developed myocardial damage manifesting in statistically significantly decreased myocardial contractility (decrease in systolic volume and cardiac output), cardiac electrical activity impairment (T-wave amplitude increase), proven lowering of exercise tolerance (swimming duration).

Following 14 days of the study drugs administration positive changes in evaluated parameters were noted. In 28 days significant improvement of the evaluated parameters was demonstrated compared to the results obtained on Day 7 (after the second isadrine injection) ($p<0.05$) (see Table 1).

TABLE 1

Changes in efficacy endpoints of CHF treatment (in % on Day 28 vs. Day 7)

| Evaluated parameter | ULD of antibodies against C-terminal fragment of human angiotensin II AT1 receptor | ULD of anti-endothelial NO synthase antibodies | Combined drug based on ULD of antibodies to C-terminal fragment of angiotensin II AT1 receptor and antibodies to endothelial NO synthase | Losartan | Distilled water |
|---|---|---|---|---|---|
| T-wave amplitude | −22.37% | −15.81% | −30.03% | −31.64% | −7.7% |
| Heart rate | −10.75% | −8.57% | −22.43% | −21.28% | −6.74% |
| Systolic volume (by Kubrick) | 46.98% | 22.62% | 69.74% | 64.01% | 15.0% |
| Cardiac output | 35.11% | 12.43% | 49.40% | 55.31% | 7.13% |

Thus, concomitant administration of the study preparations of ULD antibodies (combined drug) proved to be more effective compared to monotherapies, increased exercise tolerance, helped normalize cardiac electrical activity and cardiac cycle, systemic and intracardiac hemodynamics in rats with CHF. ULD antibodies combination demonstrated non-inferiority in terms of efficacy compared to losartan.

Example 2

Double blind, placebo-controlled clinical study of a combination of activated potentiated forms of antibodies to the C-terminal fragment of the angiotensin II AT1 receptor, in a mixture of homeopathic dilutions of C12, C30, C200, with activated potentiated form of antibodies to endothelial NO-synthase, in a mixture of homeopathic dilutions of C12, C30, C200, in human patients with chronic heart failure to evaluate key parameters of the CHF pathology.

80 patients (CHF of II-IV functional class (FC), left ventricular ejection fraction (LVEF) less than 40%) were divided in 4 equal treatment and control groups for a 6 months study. The background therapy was not discontinued (β-blocker bisoprolol, ACE inhibitor enalapril, aspirin (unless contraindicated); administration of diuretics, nitrates, digoxin was also admitted). Group 1 received the activated potentiated form of antibodies to a C-terminal fragment of the angiotensin II AT1 receptor (mixture of homeopathic dilutions C12, C30, C200) (3 tablets/day, n=20). Group 2 received the activated potentiated form of antibodies to endothelial NO-synthase (mixture of homeopathic dilutions C12, C30, C200) (3 tablets/day, n=20). Group 3 received the combination pharmaceutical composition comprising both activated potentiated form of antibodies to a C-terminal fragment of angiotensin II AT1-receptor (mixture of homeopathic dilutions C12, C30, C200) and activated potentiated form of antibodies to endothelial NO-synthase (mixture of homeopathic dilutions C12, C30, C200) (3 tablets/day, n=20). Group 4 received placebo (3 tablets/day, n=20) The groups were comparable in the initial study parameters: in age and sex, and severity (class of CHF and LVEF) and duration of the disease.

Before and after treatment, the patients were evaluated for the effect of the administered medications on vascular remodeling and endothelium dysfunction that is important for the CHF process and progression. The effects of the medications on the processes of vascular remodeling were evaluated by pulse wave velocity (PWV) ("Colson" system) in the carotid-femoral (CF) (elastic type) and carotid-radial (CR) (muscle type) segments of arteries.

Table 2 shows the dynamics in the rates of pulse wave velocity in the carotid-femoral (CF) (elastic type) and carotid-radial (CR) (muscle type) segments of arteries.

TABLE 2

| Groups/Parameters | ULDs[1] of Abs[2] to C-terminal fragment of AT1 receptor of angiotensin II | | | ULD of Abs to endothelial NO-synthase | | | Combination of ULDs of Abs to C-end fragment of AT1 receptor of angiotensine II and ULD of Abs to endothelial NO-synthase | | | Placebo | | |
|---|---|---|---|---|---|---|---|---|---|---|---|---|
| | ^ | & | Δ% | ^ | & | Δ% | ^ | & | Δ% | ^ | & | Δ% |
| CF, m/c | 9.7 ± 0.5 | 8 ± 0.6 | −14.8 * | 10.1 ± 0.5 | 9.8 ± 0.4 | −2.97 | 10.8 ± 0.3 | 8.6 ± 0.6 | −20.3 * | 8.2 ± 0.4 | 8.2 ± 0.5 | 0.1 |
| CR, m/c | 8.6 ± 0.2 | 8.9 ± 0.3 | 2.9 | 8.8 ± 0.1 | 8.3 ± 0.3 | −5.7 | 8.9 ± 0.5 | 7.6 ± 0.7 | −15.6 * # $ | 9.1 ± 0.3 | 9.7 ± 0.3 | 6.4 * |

^ denotes initial value
& denotes 6 month after beginning of administration
* denotes difference from initial value is verifiable with p value <0.05.
denotes difference from the group receiving ULDs of Abs to C-terminal fragment AT1 receptor angiotensin II with verifiable difference in p value of <0.05.
$ denotes difference from the group receiving ULDs of Abs to endothelial NO-synthase with significant difference in p value of <0.05.
[1] ULD denotes ultra-low doses.
[2] Abs denotes antibodies.

After 6 months of treatment, only group 3 showed a proven effect of the claimed pharmaceutical composition on the stiffness of muscular type arteries. Group 1 which received ULD of antibodies to a C-terminal fragment of angiotensin II AT1 receptor, and group 3 which received the combination pharmaceutical composition of the invention showed a proven increase in the stiffness of elastic type arteries.

Example 3

Double blind, placebo-controlled clinical study of a combination of activated potentiated forms of antibodies to the C-terminal fragment of angiotensin II AT1 receptor, in a mixture of homeopathic dilutions of C12, C30, C200, with activated potentiated form of antibodies to endothelial NO-synthase, in a mixture of homeopathic dilutions of C12, C30, C200, in human patients with chronic heart failure to evaluate key measurement of quality of life.

80 patients (CHF of II-IV functional class (FC), left ventricular ejection fraction (LVEF) less than 40%) were divided in 4 equal treatment and control groups for a 6 months study. The background therapy was not discontinued (bisoprolol β-blocker, ACE inhibitor enalapril, aspirin (unless contraindicated); administration of diuretics, nitrates, digoxin was also admitted). Group 1 received the activated potentiated form of antibodies to a C-terminal fragment of angiotensin II AT1 receptor (mixture of homeopathic dilutions C12, C30, C200) (3 tablets/day, n=20). Group 2 received the activated potentiated form of antibodies to endothelial NO-synthase (mixture of homeopathic dilutions C12, C30, C200) (3 tablets/day, n=20). Group 3 received the combination pharmaceutical composition comprising both activated potentiated form of antibodies to a C-terminal fragment of angiotensin II AT1 receptor (mixture of homeopathic dilutions C12, C30, C200) and activated potentiated form of antibodies to endothelial NO-synthase (mixture of homeopathic dilutions C12, C30, C200) (3 tablets/day, n=20). Group 4 received placebo (3 tablets/day, n=20). The groups were comparable in the initial study parameters: in age and sex, and severity (class of CHF and LVEF) and duration of the disease. Before and after treatment, the patients were evaluated for the life quality (Minnesota and Kansas questionnaires), morphological parameters of the heart, and tolerance to physical exercise.

Table 3 shows the results of the study in the form of dynamics in the basic parameters of the treatment efficacy.

After 6 months of treatment, the patients in group 1 treated with ULD of antibodies to a C-terminal fragment of angiotensin II AT1 receptor showed a significant improvement of the life quality, improvement of the left ventricular systolic function, and an increased tolerance to physical exercise. Group 2 showed a proven decrease in the anxiety and depression levels and in the life quality, which were evaluated using the Kansas questionnaire. The study confirmed that the maximum therapeutic effect was achieved with the combination pharmaceutical composition of the invention in combination with the standard CHF therapy, which was administered to patients from group 3 that showed a proven positive dynamics in all parameters under study.

The combination of activated (potentiated) forms of antibodies to a C-terminal fragment of angiotensin II AT1 receptor and to endothelial nitric oxide synthase (NO-synthase) in the pharmaceutical composition of the invention (combination drug) provides an unexpected synergistic therapeutic effect implying an enhanced influence on vascular remodeling and endothelium dysfunction that is critical for the CHF process and progression, as also on the improvement of the patients' life quality, on morphological parameters of the heart and tolerance to physical exercise, which is confirmed by clinical trials. The results are set forth in Table 3.

TABLE 3

| Groups/Parameters | ULD [1] of Abs [2] to C-terminal fragment of AT1 receptor of angiotensin II | | | ULD of Abs to endothelial NO-synthase | | |
|---|---|---|---|---|---|---|
| | ^ | & | Δ % | ^ | & | Δ % |
| Minnesota [3] | 47.5 ± 2.8 | 39.1 ± 3.8 ** | −17.6 | 48.1 ± 3.7 | 40.8 ± 3.8 | −15.2 |
| Kansas [4] | 82.1 ± 2.3 | 70.1 ± 5.5 *** | −14.6 | 81.5 ± 2.5 | 72.0 ± 8.2 * | −11.7 |
| HADS [5] | 15.3 ± 1.0 | 12.5 ± 0.9 ** | −18.5 | 16.2 ± 1.7 | 11.34 ± 2.1 *** | −30.3 |
| FC CHF [6] | 2.7 ± 0.1 | 2.2 ± 0.1 *** | −17.3 | 2.9 ± 0.1 | 2.7 ± 0.2 | −7.3 |
| FF LV [7] | 27.1 ± 0.9 | 33.6 ± 1.5 ** | 24.0 | 28.2 ± 1.5 | 25.3 ± 1.7 | 10.3 |
| 6-minute walk test | 378.7 ± 12.4 | 419.6 ± 13.7 *** | 10.8 | 383.1 ± 15.3 | 416.8 ± 17.2 | 8.8 |

| Groups/Parameters | Combination of ULD of Abs to C-terminal fragment of AT1 receptor of angiotensin II and ULD of Abs to endothelial NO-synthase | | | Placebo | | |
|---|---|---|---|---|---|---|
| | ^ | & | Δ % | ^ | & | Δ % |
| Minnesota [3] | 43.9 ± 2.8 | 32.0 ± 4.9 *** $ | −27.1 | 48.3 ± 3.7 | 42.4 ± 2.9 ** | −12.2 |
| Kansas [4] | 87.7 ± 2.3 | 65.7 ± 7.3 *** $ | −25.1 | 83.8 ± 3.5 | 60.3 ± 6.8 | −7.2 |
| HADS [5] | 16.2 ± 1.3 | 8.4 ± 0.9 *** # $$ | −48.1 | 17.3 ± 1.1 | 15.9 ± 1.1 | −8.1 |
| FC CHF [6] | 3.0 ± 0.2 | 1.9 ± 0.1 *** # $ | −36.6 | 2.7 ± 0.1 | 2.5 ± 0.1 | −6.2 |
| FF LV [7] | 25.3 ± 1.1 | 34.6 ± 1.9 *** # $ | 36.7 | 26.4 ± 1.1 | 28. ± 1.4 | 6.3 |
| 6-minute walk test | 378.7 ± 12.4 | 450.1 ± 17.7 ** # $ | 18.9 | 390.5 ± 11.9 | 409.1 ± 11.5 | 4.8 |

*, , * - p values < 0.05, 0.01 and 0.001, respectively
- difference from group receiving ULDs of Abs to C-terminal fragment AT1 of angiotensin receptor II with verifiable with p value <0.05
$, $$ - difference from the group receiving ULDs of Abs to endothelial NO- synthase is significant at p values of 0.05 and 0.01, respectively.
[1] -ULD means ultra low doses
[2] Abs means antibodies
[3] "Minnesota" denotes Minnesota Questionnaire
[4] "Kansas" denotes Kansas Questionnaire
[5] HADS denotes HADS total score
[6] FC CHF denotes patients with chronic heart failure, functional class
[7] FF LV denotes fraction of functioning of left vertical.

Example 4

Double blind placebo-controlled randomized clinical study of combination of the activated potentiated forms of antibodies to a C-terminal fragment of angiotensin II AT1 receptor, in a mixture of homeopathic dilutions of C12, C30, C200, with activated potentiated form of antibodies to endothelial NO-synthase, in a mixture of homeopathic dilutions of C12, C30, C200, in human patients with vegeto-vascular dystonia.

The clinical efficiency and safety of the combination pharmaceutical composition comprising activated-potentiated forms of antibodies to a C-terminal fragment of angiotensin II AT1 receptor and to endothelial NO-synthase (the mixtures of homeopathic dilutions C12, C30, C200) were tested on 60 male and female patients (male—26.7% (n=16), female—73.3% (n=44) of the total quantity of patients) with asthenia (more than 12 points according to "general asthenia" claim of the subjective asthenia scale MFI-20 (Multidimensional Fatigue Inventory)) and neurocirculatory asthenia (more than 15 points on the vegetative changes scale) aged 29-64 (average age 47.1±1.77 years old).

The patients were randomized in two groups (n=30 each). The first group of patients received the combination pharmaceutical composition three times a day (1 pill each time). The second group patients took the placebo tablets three times a day (1 pill each time). The overall time of administration and patients monitoring lasted for 6 months.

The efficiency of treatment was evaluated by dynamics in the parameters of the subjective asthenia scale, questionnaires for estimating the anxiety and depression levels (Spielberger and Beck scale), questionnaire for evaluating the sleep and vegetative changes.

The dynamics in the vegetative and psychological state changes, in the patients' life quality during the treatment is shown in the Table 4.

| Parameter | Combined Medication, n = 30 | | | |
|---|---|---|---|---|
| | Visit 1 | Visit 2 (4 weeks) | Visit 3 (12 weeks) | Visit 4 (24 weeks) |
| General asthenia (MFI-20 scale) (M ± m) | 12.9 ± 0.21 | 12.3 ± 0.29 | 11.5 ± 0.35 *** # | 10.9 ± 0.27 *** ## |
| Physical asthenia (MFI-20 scale) (M ± m) | 12.3 ± 0.56 | 11.7± 0.49 ** | 11.2 ± 0.45 ** | 10.2 ± 0.39 *** # |
| Hypoactivity (MFI-20 scale) (M ± m) | 10.3 ± 0.50 | 10.1 ± 0.47 | 9.5 ± 0.42 * | 9.1 ± 0.28 * |
| Motivation decrease (MFI-20 scale) (M ± m) | 9.60 ± 0.55 | 9.5 ± 0.47 | 8.6 ± 0.32 * | 8.3 ± 0.27 * |
| Psychic asthenia (MFI-20 scale) (M ± m) | 10.2 ± 0.47 | 9.7 ± 0.44 * | 9.5 ± 0.42 * | 8.9 ± 0.41 ** # |
| Questionnaire of vegetative changes (total rate) (M ± m) | 28.9 ± 1.66 | 25.3 ± 1.26 ** | 22.1 ± 1.26 *** | 17.6 ± 0.76 *** # |
| Questionnaire of sleep evaluation (total rate) | 16.9 ± 0.44 | 18.4 ± 0.42 ** | 18.9 ± 0.34 *** | 19.4 ± 0.29 *** # |
| Individual anxiety (Spielberger scale) (M ± m) | 37.6 ± 2.03 | 35.6 ± 1.42 * | 35.1 ± 1.64 ** | 32.9 ± 1.23 *** |
| Reactive anxiety (Spielberger scale) (M ± m) | 39.3 ± 1.02 | 35.7 ± 0.72 *** # | 34.5 ± 1.02 *** | 32.4 ± 0.76 *** # |
| Beck questionnaire of depression (total rate) (M ± m) | 9.2 ± 0.44 | 8.4 ± 0.25 * | 8.3 ± 0.27 * | 7.8 ± 0.31 ** # |

| Parameter | Placebo, n = 30 | | | |
|---|---|---|---|---|
| | Visit 1 | Visit 2 (4 weeks) | Visit 3 (12 weeks) | Visit 4 (24 weeks) |
| General asthenia (MFI-20 scale) (M ± m) | 13.1 ± 0.26 | 12.9 ± 0.23 | 12.5 ± 0.17 *** | 11.9± 0.19 *** |
| Physical asthenia (MFI-20 scale) (M ± m) | 12.3 ± 0.38 | 12.1 ± 0.29 | 11.7± 0.29 ** | 11.4± 0.21 ** |
| Hypoactivity (MFI-20 scale) (M ± m) | 10.6 ± 0.63 | 10.1 ± 0.53 * | 9.7 ± 0.50 ** | 9.5 ± 0.38 ** |
| Motivation decrease (MFI-20 scale) (M ± m) | 9.9 ± 0.75 | 9.7 ± 0.57 | 9.4 ± 0.51 | 9.3 ± 0.48 |
| Psychic asthenia (MFI-20 scale) (M ± m) | 10.8 ± 0.51 | 10.6 ± 0.43 | 10.5 ± 0.40 | 10.3 ± 0.38 |
| Questionnaire of vegetative changes (total rate) (M ± m) | 32.1 ± 3.36 | 29.5 ± 2.57 * | 25.9 ± 2.42 *** | 22.4 ± 2.08 *** |
| Questionnaire of sleep evaluation (total rate) | 16.6 ± 0.67 | 17.5 ± 0.56 ** | 18.1 ± 0.47 *** | 18.2 ± 0.47 *** |
| Individual anxiety (Spielberger scale) (M ± m) | 39.1 ± 3.05 | 38.7 ± 2.78 | 36.9 ± 2.45 * | 36.9 ± 2.46 * |
| Reactive anxiety (Spielberger scale) (M ± m) | 42.7 ± 2.65 | 40.3 ± 1.99 ** | 38.3 ± 1.87 ** | 37.6 ± 1.81 ** |
| Beck questionnaire of depression (total rate) (M ± m) | 11.1 ± 1.43 | 10.5 ± 1.19 * | 10.0 ± 0.93 | 9.9 ± 0.90 * | differences are significant vs the initial values at:
* $p < 0.05$,
** $p < 0.01$,
*** $p < 0.001$.
differences are significant vs placebo group:
$p < 0.05$,
$p < 0.01$,
$p < 0.001$.

It is shown that the administration of the combination pharmaceutical composition during 6 months resulted in a statistically significant decrease in the asthenia level on all MFI-20 subscales. The most significant improvements were observed in the following areas: general asthenia (from 12.9±0.21 to 10.9±0.27 points, p<0.01 of the placebo group), physical asthenia (from 12.3±0.56 to 10.2±0.39 points, p<0.05 of the placebo group), psychic asthenia (from 10.2±0.47 to 8.9±0.41 points, p<0.05 of the placebo group). After one month of treatment, basic group 1 showed a statistically proven decrease in the intensity of vegetative changes (according to the special-purpose questionnaire data), and after six months of treatment there was a statistically significant (p<0.05) difference of the achieved results (decrease of the total rate from 28.9±1.66 to 17.6±0.76) in comparison with the placebo group (decrease of the total rate from 32.1±3.36 to 22.4±2.08).

In addition, the administration of the combination pharmaceutical composition contributed to improving the psychological state of the patients in the study. A statistically significant decrease in the anxiety and depression levels was observed after one month of administration, and when the treatment was continued the positive effect was enhanced. After six months, group 1 showed a statistically significant (p<0.05) improvement in the reactive anxiety level on the Spielberger scale (decrease from 39.3±1.02 to 32.4±0.76) and the depression level according to the Beck questionnaire (decrease from 9.2±0.44 to 7.8±0.31) in comparison with the respective parameters of the placebo group (decrease from 42.7±2.65 to 37.6±1.81 and from 11.1±1.43 to 9.9±0.90 respectively). The results were confirmed by the positive dynamics (p<0.001 of the initial rates) in the parameters of the sleep evaluation questionnaire, and after six months of treatment, group 1 showed a statistically significant (p<0.05) difference in the total rate (increase from 16.9±0.44 to 19.4±0.29) in comparison with the placebo group (increase from 16.6±0.67 to 18.2±0.47).

Over the entire period of monitoring, the patients showed a high tolerability and no adverse effects.

The study showed that the combination pharmaceutical composition used in the study possesses antiasthenic effect, normalizes the vegetative state of patients with neurocirculatory dystonia and asthenia, and has anti-anxiety and anti-depression influence in the relevant patient population.

Example 5

Study of the combination of activated-potentiated forms of antibodies to the C-terminal fragment of the angiotensin II AT1 receptor, in a mixture of homeopathic dilutions of C12, C30, C200, with the activated-potentiated form of antibodies to endothelial NO synthase, in a mixture of homeopathic dilutions of C12, C30, C200, in SHR rats in a model of hypertension. The combination of water solution of the activated-potentiated form of antibodies to a C-terminal fragment of the angiotensin II AT1 receptor, in a mixture of homeopathic dilutions of C12, C30, C200, and the activated-potentiated form of antibodies to endothelial NO synthase in a mixture of homeopathic dilutions of C12, C30, C200, was studied in the SHR rat hypertension model. Investigations were conducted on 40 SHR line male rats from (weight 350±50 g, age 4.5-5 months) with hypertension, which were divided into 4 groups of 10 animals each.

For 28 days, the animals were treated as follows. Group 1 —2.5 ml/kg of the activated-potentiated form of antibodies to the C-terminal fragment of human angiotensin II AT1 receptor (a mixture of aqueous dilutions C12, C30, C200) in combination with 2.5 ml/kg of distilled water, Group 2 —2.5 ml/kg of the activated-potentiated form of antibodies to endothelial NO synthase (a mixture of aqueous dilutions C12, C30, C200) in combination with 2.5 ml/kg of distilled water, Group 3 —5 ml/kg of the combination pharmaceutical composition (a mixture of aqueous dilutions C12, C30, C200 for each component), and Group 4 —5 ml/kg of distilled water.

Systolic blood pressure (SBP) of awake rats was measured with the aid of an indirect method in a tail artery (using a cuff) once a week and 9 hours after the last administration of medicines.

All tested compositions demonstrated hypotensive effect (p<0.05): by $28^{th}$ day, systolic blood pressure (SBD) decreased in comparison with the initial level in Group 1 by—20.6%; in Group 2 by 14.4%; in Group 3 by 27.6%. In the control Group 4, SBD changes were 1.6% in comparison with the initial values. The results demonstrate a clear synergistic hypotensive effect of the combination pharmaceutical composition.

Example 6

Study of the combination of the activated-potentiated forms of antibodies to a C-terminal fragment of angiotensin II AT1 receptor, in a mixture of homeopathic dilutions of C12, C30, C200, with the activated-potentiated form of antibodies to endothelial NO synthase, in a mixture of homeopathic dilutions of C12, C30, C200, in NISAG rats in a model of hypertension.

The combination water solution of the activated potentiated form of antibodies to a C-terminal fragment of angiotensin II AT1 receptor, in a mixture of homeopathic dilutions of C12, C30, C200, and the activated potentiated form of antibodies to endothelial NO synthase in a mixture of homeopathic dilutions of C12, C30, C200, was studied in the NISAG rat hypertension model. Investigations were conducted on 50 NISAG line male rats (weight 300 g, age 4 months) with hereditary stipulated stress-sensitive arterial hypertension, which were divided into 5 groups by 10 animals each.

The animals were given per orally, once a day and for 28 days, the following medications: Group 1—2.5 ml/kg of the activated-potentiated form of antibodies to a C-terminal fragment of human angiotensin II AT1 receptor (a mixture of dilutions C12, C30, C200) in combination with 2.5 ml/kg of distilled water; Group 2—2.5 ml/kg of the activated-potentiated form of antibodies to endothelial NO synthase (a mixture of dilutions C12, C30, C200) in combination with 2.5 ml/kg of distilled water; Group 3-5 ml/kg of the combination pharmaceutical composition (a mixture of homeopathic aqueous dilutions C12, C30, C200 of each component); Group 4-5 ml/kg (10 ml/kg dose) of the comparison drug (losartan); and Group 5-5 ml/kg of distilled water.

Two times a week, 2 to 6 hours after administration of ULD antibodies and losartan, systolic blood pressure (SBP) was measured by an indirect method in a tail artery (using a cuff). The Table 5 shows the dynamics of changes in systolic blood pressure in NISAG line rats, measured by indirect method.

TABLE 5

|  | Initial SBP in mmHg | SBP after 28 days of medicine administration in mmHg | Δ in comparison with the initial level, in mmHg | % of the initial level |
|---|---|---|---|---|
| ULD antibodies to C-terminal fragment of angiotensin II AT1receptor | 176 | 150 | −26 | −14.7% |
| ULD antibodies to endothelial NO synthase | 175 | 164.5 | −10.5 | −6% |
| ULD antibodies to C-terminal fragment of angiotensin II AT1receptor and to endothelial NO synthase | 179.5 | 140 | −39.5 | −22% |
| Losartan | 173.5 | 140.5 | −33 | −19% |
| Control (distilled water) | 181 | 178 | −3 | −1.6% |

Example 7

Study of Correction of Endothelial Dysfunction

Wistar rats weighed 250-300 g were divided into 4 groups. The $1^{st}$ group received distilled water 9 ml/kg/day (every day, gastrointestinal introduction). The 2nd group received L-NAME (L-NG-nitroarginine methyl ester, which is known to inhibit endothelial isoform, and thus is believed to simulate endothelial dysfunction) at 12.5 mg/kg. The third group received L-NAME (12.5 mg/kg) in combination with a mixture of C12, C30, and C200 homeopathic dilutions of polyclonal rabbit antibodies to human endothelial NO synthase at 9 ml/kg/day. The 4$^{th}$ group received L-NAME (12.5 mg/ml) in combination with a mixture of C12, C30, and C200 homeopathic dilutions of polyclonal rabbit antibodies to human endothelial NO synthase at 9 ml/kg/day and mixture of C12, C30, C200 homeopathic dilutions of polyclonal rabbit antibodies to a C-terminal fragment of AT1 receptor of angiotensin II at 9 ml/kg/day.

Endothelial dysfunction was simulated by introducing L-NAME at 12.5 mg/ml/day in the course of 28 days. On day 29 from the beginning of the experiment, under anesthesia (sodium thiopental at 50 mg/kg), a catheter was inserted into the left carotid artery to register parameter of arterial pressure (AP). Bolus introduction of the pharmacological agent was made into right femoral vein. The following parameters were measured: systolic arterial pressure (SAP), diastolic arterial pressure (DAP), and frequency of heart beat, which were measured in real time by sensor TSD104A measurement apparatus MP100 made by Biopac System, Inc., USA. The following functional probes were used: endothelium-dependent vasodilation (EDV), intra-vein introduction of acetylcholine (AC) in the dose of 40 μg/kg, endothelium-independent vasodilation (EIV) via intravein introduction of sodium nitroprusside at 30 μ/kg.

The degree of endothelial dysfunction was evaluated via the coefficient of endothelial dysfunction as the ratio of the area of the triangle under the trend of reaction of stabilization of arterial pressure (AP) as a response to introduction of nitroprusside to the area of the triangle under the trend of reaction of stabilization of arterial pressure as a response to introduction of acetylcholine.

The results of the experiments are presented in Table 6.

TABLE 6

| Groups | Functional Probe | SAP, mm, HG | DAP, mm HG | Vascular reaction observed with EDV with acetyl choline EIV with sodium nitroprusside | CED, (relative units) |
|---|---|---|---|---|---|
| Control (daily in-stomach introduction of distilled water at 9 ml/kg/day | Initial | 159.2 ± 5.4 | 124.2 ± 4.7 |  | 1.2 ± 0.1 |
|  | Acetyl choline | 96.9 ± 6.7 | 52.0 ± 3.0 | 3071.2 ± 501.1 |  |
|  | Sodium Nitroprusside | 113.8 ± 6.1 | 55 ± 2.4 | 3617.2 ± 560.1 |  |
| L-NAME | Initial | 204.8 ± 10* | 164.2 ± 5.9* |  | 3.5 ± 0.5* |
|  | Acetyl choline | 111.3 ± 7.4 | 64.7 ± 4.3* | 3700.2 ± 536.9 |  |
|  | Sodium Nitroprusside | 118.2 ± 9.9 | 61.4 ± 4.4 | 11922.8 ± 1838.9* |  |
| L-NAME in combination with a mixture of C12, C30, and C200 homeopathic dilutions of polyclonal rabbit antibodies to human endothelial NO-synthase | Initial | 230.1 ± 8.8* | 175.1 ± 6.4* |  | 1.8 ± 0.2** |
|  | Acetyl choline | 116.4 ± 4.0* | 73.5 ± 3.5* | 5826.0 ± 801.2** |  |
|  | Sodium Nitroprusside | 108.1 ± 4.6 | 60 ± 3.6 | 9628.5 ± 970.1* |  |
| L-NAME in combination with a mixture of C12, C30, and C200 homeopathic dilutions of polyclonal rabbit antibodies to human endothelial NO-synthase and mixture of C12, C30, C200 homeopathic dilutions of polyclonal rabbit antibodies to C-terminal fragment of AT1 receptor of angiotensin II | Initial | 213.6 ± 4.6* | 166.8 ± 2.7* |  | 1.4 ± 0.1** |
|  | Acetyl choline | 116.9 ± 5.5* | 73.3 ± 3.4* | 3295.3 ± 201.4 |  |
|  | Sodium Nitroprusside | 122.3 ± 4.6 | 70.5 ± 4.5* | 4546.2 ± 299.4** |  |

*p < 0.05 in comparison with the control group;
**p < 0.05 in comparison with the L-NAME group.
S—area under the curve of restoration of arterial hypertension per pharmacological probes,,
CED—coefficient of endothelial dysfunction.

What is claimed is:

1. A combination pharmaceutical composition for administration to a patient associated with at least one symptom of at least one condition selected from the group consisting of chronic heart failure, asthenia, vegetative vascular dystonia, anxiety associated with chronic heart failure, depression associated with chronic heart failure and hypertension, the combination pharmaceutical composition comprising a) an activated-potentiated form of an antibody to angiotensin II AT1 receptor, and b) an activated-potentiated form of an antibody to endothelial NO-synthase, the activated potentiated forms produced by homeopathic technology.

2. The combination pharmaceutical composition of claim 1, wherein said activated-potentiated form of an antibody to angiotensin II AT1 receptor is an activated-potentiated form of an antibody to the C-terminal fragment of the angiotensin II AT1 receptor.

3. The combination pharmaceutical composition of claim 1, wherein said pharmaceutical composition is administered to said patient suffering from a condition associated with a reduced quality of life and wherein said administration of said pharmaceutical composition to said patient improves said quality of life of said patient.

4. The combination pharmaceutical composition of claim 1, wherein said activated-potentiated form of an antibody to angiotensin II AT1 receptor is in the form of a C12, C30, or C200 homeopathic dilution or a mixture thereof.

5. The combination pharmaceutical composition of claim 1, wherein said activated-potentiated form of an antibody to angiotensin II AT1 receptor is in the form of a mixture of C12, C30, and C200 homeopathic dilutions impregnated onto a solid carrier.

6. The combination pharmaceutical composition of claim 1, wherein said activated-potentiated form of an antibody to endothelial NO-synthase is in the form of a C12, C30, or C200 homeopathic dilution or a mixture thereof.

7. The combination pharmaceutical composition of claim 1, wherein said activated-potentiated form of an antibody to endothelial NO-synthase is in the form of mixture of C12, C30, and C200 homeopathic dilutions impregnated onto a solid carrier.

8. The combination pharmaceutical composition of claim 1, which is prepared by impregnating a solid carrier with a mixture of i) said activated-potentiated form of an antibody to endothelial NO-synthase is in the form of mixture of C12, C30, and C200 homeopathic dilutions, and ii) said activated-potentiated form of an antibody to angiotensin II AT1 receptor is in the form of mixture of C12, C30, and C200 homeopathic dilutions.

9. The combination pharmaceutical composition of claim 1, wherein said activated-potentiated form of an antibody to angiotensin II AT1 receptor is a monoclonal, polyclonal or natural antibody.

10. The combination pharmaceutical composition of claim 9, wherein said activated-potentiated form of an antibody to angiotensin II AT1 receptor is a polyclonal antibody.

11. The combination pharmaceutical composition of claim 8, wherein said activated-potentiated form of an antibody to angiotensin II AT1 receptor is prepared by successive centesimal homeopathic dilutions coupled with shaking of every dilution.

12. The combination pharmaceutical composition of claim 1, wherein said activated-potentiated form of an antibody to endothelial NO-synthase is a monoclonal, polyclonal or natural antibody.

13. The combination pharmaceutical composition of claim 12, wherein said activated-potentiated form of an antibody to endothelial NO-synthase is a polyclonal antibody.

14. The combination pharmaceutical composition of claim 8, wherein said activated-potentiated form of an antibody to endothelial NO-synthase is prepared by successive centesimal homeopathic dilutions coupled with shaking of every dilution.

15. A method of treating a patient suffering from a reduced overall quality of life associated with at least one symptom of at least one condition selected from the group consisting of chronic heart failure, asthenia, vegetative vascular dystonia, anxiety associated with chronic heart failure, depression associated with chronic heart failure and hypertension, the combination pharmaceutical composition comprising administering to said patient substantially at the same time a) an activated-potentiated form of an antibody to angiotensin II AT1 receptor, and b) an activated-potentiated form of an antibody to endothelial NO-synthase, the activated potentiated forms produced by homeopathic technology, thereby said administration improves said overall quality of life of said patient.

16. The method of claim 15, wherein said activated-potentiated form of an antibody to angiotensin II AT1 receptor is an activated-potentiated form of an antibody to the C-terminal fragment of the angiotensin II AT1 receptor.

17. The method of claim 15 wherein said a) an activated-potentiated form of an antibody to angiotensin II AT1 receptor, and b) an activated-potentiated form of an antibody to endothelial NO-synthase are administered in the form of a combined pharmaceutical composition.

18. The method of claim 15, further comprising concomitantly administering to said patient an additional therapeutic agent.

19. The method of claim 18, wherein said additional therapeutic agent is selected from the group consisting of ACE inhibitors, diuretics; β-adrenergic blockers, nitrates, cardiac glycosides, calcium antagonists, hypolipidemic agents, antiaggregants, antihypoxants, and anticoagulants.

20. The method of claim 19, wherein said additional therapeutic agent is bisoprol, enalapril or aspirin.

21. The method of claim 15 wherein said patient is administered said composition in the form of a solid unit dosage form comprising said activated-potentiated form of an antibody to angiotensin II AT1 receptor and said activated-potentiated form of an antibody to endothelial NO-synthase.

22. The method of claim 21, wherein said patient is administered one to two of said unit dosage forms, each administration carried out from once daily to four times daily.

23. The method of claim 15, which comprises administration of from one to two unit dosage forms of said activated-potentiated form of an antibody to angiotensin II AT1 receptor, and from one to two unit dosage forms of said activated-potentiated form of an antibody to endothelial NO-synthase, each of said dosage forms being administered from once daily to four times daily.

24. The method of claim 23, wherein each of said unit dosage forms is administered twice daily.

25. The method of claim 15, wherein said reduced overall quality of life is associated with at least one symptom of chronic heart failure.

26. The method of claim 25, wherein said patient exhibits statistically significant improvement in rigidity parameters of carotid radial artery segments upon said administration.

27. The method of claim 15, wherein said reduced overall quality of life is associated with at least one symptom of asthenia and/or vegetative vascular dystonia.

28. The method of claim 27, wherein said administration of said combination leads to a statistically significant improvement in the mental asthenia by the MFI-20 scale in a suitable population of said patients in reference to the baseline.

29. The method of claim 27, wherein said administration of said combination leads to a statistically significant reduction in the general asthenia by the MFI-20 scale in a suitable population of said patients in reference to the baseline.

30. The method of claim 15, wherein said reduced overall quality of life is associated with anxiety related to one or more symptoms of a health condition.

31. The method of claim 30, wherein said administration of said combination leads to a statistically significant improvement in the Minnesota Total Inventory Score in a suitable population of said patients in reference to the baseline.

32. The method of claim 15, wherein said reduced overall quality of life is associated with depression related to one or more symptoms of a health condition.

33. The method of claim 32, wherein said administration of said combination leads to a statistically significant reduction in the Beck Questionnaire Score in a suitable population of said patients in reference to the baseline.

34. The method of claim 15, wherein said activated-potentiated form of an antibody to angiotensin II AT1 receptor is a monoclonal, polyclonal or natural antibody.

35. The method of claim 15, wherein said activated-potentiated form of an antibody to angiotensin II AT1 receptor is a polyclonal antibody.

36. The method of claim 15, wherein said activated-potentiated form of an antibody to endothelial NO-synthase is a monoclonal, polyclonal or natural antibody.

37. The method of claim 15, wherein said activated-potentiated form of an antibody to endothelial NO-synthase is a polyclonal antibody.

38. A method of treating a patient suffering from chronic heart failure, said method comprising administering to said patient a combination of a) an activated-potentiated form of an antibody to angiotensin II AT1 receptor, and b) an activated-potentiated form of an antibody to endothelial NO-synthase, the activated potentiated forms produced by homeopathic technology.

39. The method of claim 38, wherein said activated-potentiated form of an antibody to angiotensin II AT1 receptor is an activated-potentiated form of an antibody to the C-terminal fragment of the angiotensin II AT1 receptor.

40. The method of claim 38, further comprising concomitant administration to said patient of an additional therapeutic agent selected from the group consisting of ACE inhibitors, diuretics; β-adrenergic blockers, nitrates, cardiac glycosides, calcium antagonists, hypolipidemic agents, antiaggregants, antihypoxants, and anticoagulants.

41. The method of claim 40, wherein said therapeutic agent is selected from bisoprol, enalapril and aspirin.

42. The method of claim 38, wherein said patient is administered said composition in the form of a solid unit dosage form comprising said activated-potentiated form of an antibody to angiotensin II AT1 receptor and said activated-potentiated form of an antibody to endothelial NO-synthase.

43. The method of claim 42, wherein said patient is administered one to two of said unit dosage forms, each administration carried out from once daily to four times daily.

44. The method of claim 38, which comprises administration of from one to two unit dosage forms of said activated-potentiated form of an antibody to angiotensin II AT1 receptor, and from one to two unit dosage forms of said activated-potentiated form of an antibody to endothelial NO-synthase, each of said dosage forms being administered from once daily to four times daily.

45. The method of claim 38, wherein said patient exhibit statistically significant improvement in rigidity parameters of carotid radial artery segments upon said administration.

46. The method of claim 45, wherein said patient exhibit statistically significant improvement in rigidity parameters of carotid femoral artery segments upon said administration.

47. The method of claim 38, wherein said patient exhibits statistically significant reduction in anxiety associated with said chronic heart failure upon said administration.

48. The method of claim 47, wherein said administration of said combination leads to a statistically significant improvement in the Minnesota Total Inventory Score in a suitable population of said patients in reference to the baseline.

49. The method of claim 47, wherein said administration of said combination leads to a statistically significant reduction in the Kansas City Cardiomyopathy Questionnaire Total Score in a suitable population of said patients in reference to the baseline.

50. The method of claim 38, wherein said administration of said combination leads to a statistically significant improvement in a 6-minute walking test score in a suitable population of said patients.

51. The method of claim 38, wherein said administration of said combination leads to a statistically significant improvement in the HADS Total score in a suitable population of said patients.

52. The method of claim 38, wherein said patient exhibits statistically significant reduction in depression associated with said chronic heart failure upon said administration.

53. The method of claim 38, wherein said activated-potentiated form of an antibody to a C-terminal fragment of the angiotensin II AT1 receptor is a monoclonal, polyclonal or natural antibody.

54. The method of claim 53, wherein said activated-potentiated form of an antibody to a C-terminal fragment of the angiotensin II AT1 receptor is a polyclonal antibody.

55. The method of claim 38, wherein said activated-potentiated form of an antibody to endothelial NO-synthase is a monoclonal, polyclonal or natural antibody.

56. The method of claim 55, wherein said activated-potentiated form of an antibody to endothelial NO-synthase is a polyclonal antibody.

57. A method of treating a patient suffering from asthenia and/or vegetative-vascular dystonia, said method comprising administering to said patient a combination of a) an activated-potentiated form of an antibody to angiotensin II AT1 receptor, and b) an activated-potentiated form of an antibody to endothelial NO-synthase, the activated potentiated forms produced by homeopathic technology.

58. The method of claim 57, wherein said activated-potentiated form of an antibody to angiotensin II AT1 receptor is an activated-potentiated form of an antibody to the C-terminal fragment of the angiotensin II AT1 receptor.

59. The method of claim 57, further comprising concomitant administration to said patient of an additional therapeutic agent selected from the group consisting of ACE inhibitors, diuretics; β-adrenergic blockers, nitrates, cardiac glycosides, calcium antagonists, hypolipidemic agents, antiaggregants, antihypoxants, and anticoagulants.

60. The method of claim 59, wherein said additional therapeutic agent is selected from bisoprol, enalapril and aspirin.

61. The method of claim 59, wherein said patient is administered said composition in the form of a solid unit dosage form comprising said activated-potentiated form of an antibody to angiotensin II AT1 receptor and said activated-potentiated form of an antibody to endothelial NO-synthase.

62. The method of claim 61, wherein said patient is administered one to two of said unit dosage forms, each administration carried out from once daily to four times daily.

63. The method of claim 59, which comprises administration of from one to two unit dosage forms of said activated-potentiated form of an antibody to angiotensin II AT1 receptor, and from one to two unit dosage forms of said activated-potentiated form of an antibody to endothelial NO-synthase, each of said dosage forms being administered from once daily to four times daily.

64. The method of claim 63, wherein said one to two unit dosage form of each of said activated-potentiated forms of antibodies is administered twice daily.

65. The method of claim 59, wherein said patient exhibit statistically significant improvement in rigidity parameters of carotid radial artery segments upon said administration.

66. The method of claim 65, wherein said patient exhibit statistically significant improvement in rigidity parameters of carotid femoral artery segments upon said administration.

67. The method of claim 57, wherein said patient exhibits statistically significant reduction in mental asthenia upon said administration.

68. The method of claim 67, wherein said administration of said combination leads to a statistically significant reduction in the mental asthenia by the MFI-20 scale in a suitable population of said patients in reference to the baseline.

69. The method of claim 57, wherein said patient exhibits statistically significant reduction in general asthenia upon said administration.

70. The method of claim 69, wherein said administration of said combination leads to a statistically significant reduction in the general asthenia by the MFI-20 scale in a suitable population of said patients in reference to the baseline.

71. The method of claim 57, wherein said patient exhibits statistically significant reduction in anxiety associated with said asthenia and/or vegetative vascular dystonia upon said administration.

72. The method of claim 71, wherein said administration of said combination leads to a statistically significant reduction in the trait anxiety as measured by Spielberg test in a suitable population of said patients in reference to the baseline.

73. The method of claim 57, wherein said patient exhibits statistically significant reduction in depression associated with said asthenia and/or vegetative vascular dystonia upon said administration.

74. The method of claim 73, wherein said administration of said combination leads to a statistically significant reduction in depression as measured by Beck test in a suitable population of said patients in reference to the baseline.

75. The method of claim 57, wherein said patient exhibits statistically significant improvement in brachial artery dilation level upon said administration.

76. The method of claim 57, wherein said activated-potentiated form of an antibody to a C-terminal fragment of the angiotensin II AT1 receptor is an antibody is a monoclonal, polyclonal or natural antibody.

77. The method of claim 76, wherein said activated-potentiated form of an antibody to a C-terminal fragment of the angiotensin II AT1 receptor is a polyclonal antibody.

78. The method of claim 77, wherein said activated-potentiated form of an antibody to a C-terminal fragment of the angiotensin II AT1 receptor is prepared by successive centesimal homeopathic dilutions coupled with vertical shaking of every dilution.

79. The method of claim 57, wherein said activated-potentiated form of an antibody to endothelial NO-synthase is an antibody is a monoclonal, polyclonal or natural antibody.

80. The method of claim 79, wherein said activated-potentiated form of an antibody to endothelial NO-synthase is a polyclonal antibody.

81. A method of treating hypertension comprising administering the combination of claim 1 to a patient in need thereof.

82. The method of claim 81, further comprising concomitant administration to said patient of an additional therapeutic agent selected from the group consisting of ACE inhibitors, diuretics; β-adrenergic blockers, nitrates, cardiac glycosides, calcium antagonists, hypolipidemic agents, antiaggregants, antihypoxants, and anticoagulants.

83. A combination pharmaceutical composition for administration to a patient suffering from at least one symptom of chronic heart failure, asthenia, vegetative dystonia, or hypertension said composition comprising, a) an activated-potentiated form of an antibody to angiotensin II AT1 receptor, and b) an activated-potentiated form of an antibody to endothelial NO-synthase, the activated potentiated forms produced by homeopathic technology.

* * * * *